United States Patent
Sparks et al.

(10) Patent No.: US 10,031,142 B2
(45) Date of Patent: Jul. 24, 2018

(54) IN SITU CHEMILUMINESCENT SUBSTRATES AND ASSAYS

(75) Inventors: Alison Sparks, North Andover, MA (US); Zhixian Wang, Winchester, MA (US); Melissa Gee, Littleton, MA (US)

(73) Assignee: Life Technologies Corporation, Carlsbad, CA (US)

( * ) Notice: Subject to any disclaimer, the term of this patent is extended or adjusted under 35 U.S.C. 154(b) by 660 days.

(21) Appl. No.: 13/808,922

(22) PCT Filed: Jul. 6, 2011

(86) PCT No.: PCT/US2011/043074
§ 371 (c)(1),
(2), (4) Date: Apr. 10, 2013

(87) PCT Pub. No.: WO2012/006351
PCT Pub. Date: Jan. 12, 2012

(65) Prior Publication Data
US 2013/0196325 A1    Aug. 1, 2013

Related U.S. Application Data

(60) Provisional application No. 61/362,608, filed on Jul. 8, 2010.

(51) Int. Cl.
G01N 33/58 (2006.01)
C12Q 1/42 (2006.01)
(Continued)

(52) U.S. Cl.
CPC ......... *G01N 33/581* (2013.01); *C07D 321/00* (2013.01); *C07F 9/12* (2013.01);
(Continued)

(58) Field of Classification Search
CPC ........ C07F 9/12; C07F 9/4056; C07F 9/6541; C07F 9/65512; C07F 9/65583;
(Continued)

(56) References Cited

U.S. PATENT DOCUMENTS 4,959,182 A    9/1990    Schaap
5,132,204 A *  7/1992    Urdea .................. C07D 321/00
                                                         252/700

(Continued)

FOREIGN PATENT DOCUMENTS

EP    0254051    1/1988
EP    0421788    4/1991
(Continued)

OTHER PUBLICATIONS

Foote et al. Olefin oxidations with excited singlet molecular oxygen. J. Am. Chem. Soc. 1964, vol. 86, pp. 3879-3880.*
(Continued)

*Primary Examiner* — Shafiqul Haq

(57) ABSTRACT

Methods for generating a chemiluminescent enzyme substrate in situ, in aqueous or other assay conditions. Also disclosed are methods to use the substrates to generate light, detect and/or quantify enzymes, antigens, and/or nucleic acids. Kits relating to these methods are also disclosed.

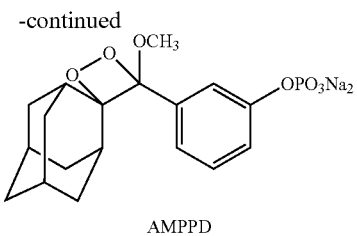

AMPPD

16 Claims, 29 Drawing Sheets

(51) Int. Cl.
| | | |
|---|---|---|
| C12Q 1/34 | (2006.01) | |
| C07F 9/12 | (2006.01) | |
| C07F 9/40 | (2006.01) | |
| C07F 9/6541 | (2006.01) | |
| C07F 9/655 | (2006.01) | |
| C07F 9/6558 | (2006.01) | |
| C07H 15/203 | (2006.01) | |
| C12Q 1/6816 | (2018.01) | |
| C07D 321/00 | (2006.01) | |

(52) U.S. Cl.
CPC .......... *C07F 9/4056* (2013.01); *C07F 9/6541* (2013.01); *C07F 9/65512* (2013.01); *C07F 9/65583* (2013.01); *C07H 15/203* (2013.01); *C12Q 1/34* (2013.01); *C12Q 1/42* (2013.01); *C12Q 1/6816* (2013.01)

(58) Field of Classification Search
CPC .......... C07H 15/203; C12Q 1/34; C12Q 1/42; C12Q 1/6816; G01N 33/581; C07D 321/00
See application file for complete search history.

(56) References Cited

U.S. PATENT DOCUMENTS

| | | | |
|---|---|---|---|
| 5,177,241 A | 1/1993 | Bronstein et al. | |
| 5,386,017 A | 1/1995 | Schaap | |
| 5,582,980 A | 12/1996 | Bronstein et al. | |
| 5,639,907 A | 6/1997 | Bronstein et al. | |
| 5,800,999 A | 9/1998 | Bronstein et al. | |
| 5,994,073 A * | 11/1999 | Bronstein | C07F 9/12 435/6.1 |
| 6,355,441 B1 | 3/2002 | Edwards et al. | |
| 6,461,876 B1 | 10/2002 | Giri | |
| 2002/0106687 A1* | 8/2002 | Bronstein | C07D 321/00 435/6.12 |
| 2003/0023089 A1 | 1/2003 | Akhavan-Tafti et al. | |

FOREIGN PATENT DOCUMENTS

| | | |
|---|---|---|
| EP | 1102067 | 5/2001 |
| WO | WO-97/26254 | 7/1997 |
| WO | WO-1998/027105 | 6/1998 |
| WO | WO-98/39471 | 9/1998 |
| WO | WO 03054506 A2 * | 7/2003 ........... C07D 321/00 |

OTHER PUBLICATIONS

PCT/US2011/043074, International Search Report and Written Opinion, dated Nov. 12, 2011.
PCT/US2011/043074, International Preliminary Report on Patentability, dated Jan. 17, 2013.
Schmidt, R. R., *Adv. Carbohydr. Chem. Biochem.*, 50, 1994, 21.
Kopecky, K. et al., "Preparation and Thermolysis of some 1,2-Dioxetanes", *Canadian Journal of Chemistry*, vol. 53, No. 8, 1975, pp. 1103-1122.

* cited by examiner

IN SITU CHEMILUMINESCENT SUBSTRATES AND ASSAYS

CROSS-REFERENCE TO RELATED APPLICATIONS

This application is a 371 of International application no. PCT/US2011/043074 filed Jul. 6, 2011 which claims priority to U.S. application No. 61/362,608 filed Jul. 8, 2010, which disclosures are herein incorporated by reference in their entirety.

FIELD OF THE INVENTION

The invention relates generally to diagnostic assays and more specifically to chemiluminescent substrates. Disclosed are methods useful for the generation of chemiluminescent substrates in situ and methods for their use in diagnostic assays.

BACKGROUND OF THE INVENTION

Clinical diagnostic assays now use chemiluminescence as the preferred state-of-the-art detection technology. Assays with chemiluminescent readouts have the most sensitive detection limits and widest dynamic range for analyte quantification. Increasingly, there is a need to design simplified, miniaturized, self-contained, and/or robust diagnostic platforms for use in the field or in developing countries, where standard lab equipment, controlled environments, and technical support are minimal. The current commercially available dioxetane substrates do not fare well where controlled storage conditions are not readily available. Thus, there is a need for a method of generating in situ dioxetane substrates using precursors which have better thermal stability.

SUMMARY OF THE INVENTION

In a first aspect, the present invention provides methods for generating light, comprising the steps of (a) providing an oxidant; (b) providing an enol ether having the structure:

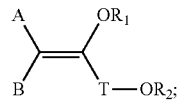

[1]

(c) combining an aqueous solution, the oxidant, and the enol ether to form an aqueous solution comprising a 1,2-dioxetane enzyme substrate; (d) providing an enzyme complex comprising an enzyme moiety which is capable of cleaving the 1,2-dioxetane enzyme substrate; (e) contacting the enzyme complex with the aqueous solution comprising the 1,2-dioxetane enzyme substrate to form a reaction mixture; and (f) allowing the reaction mixture to generate light.

The oxidant may be selected from hydrogen peroxide, sodium molybdate, hydrogen peroxide and sodium molybdate, hypochlorite, hypochlorite and hydrogen peroxide, aryl endoperoxide, calcium peroxide peroxyhydrate, and combinations thereof. In some embodiments, the oxidant may be hydrogen peroxide, or hydrogen peroxide and sodium molybdate.

In the enol ether [1], A and B may be independently selected from the group consisting of straight chain alkyl containing 1 to 20 carbon atoms, straight chain alkenyl containing 2 to 20 carbon atoms, branched alkyl containing 3 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms and polycycloheteroalkenyl containing 4 to 60 carbon atoms, any of which can be unsubstituted or substituted with one or more electron-active groups, solubilizing groups, or light-enhancing groups, and where A and B together form the cycloalkyl, cycloalkenyl, polycycloalkyl or polycycloalkenyl, one of the carbon atoms of the cycloalkyl, cycloalkenyl, polycycloalkyl, or polycycloalkenyl is one of two carbon atoms forming the double bond of the enol ether, $R_1$ may be alkyl containing 1 to 20 carbon atoms, aryl containing 6 to 14 carbon atoms, aralkyl containing 7 to 15 carbon atoms, heteroaryl containing 4 to 20 carbon atoms, or heteroaralkyl containing 5 to 20 carbons, T may be an aryl or heteroaryl ring capable of emitting light, and $R_2$ may be an enzyme-cleavable group that contains a bond cleavable by an enzyme moiety to yield an oxygen anion on T.

In some embodiments, the enol ether may have at least one of A or B which is

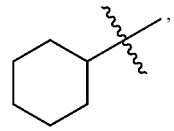 [SMILES: "," ; *C1CCCCC1]

while in other embodiments, A and B together is

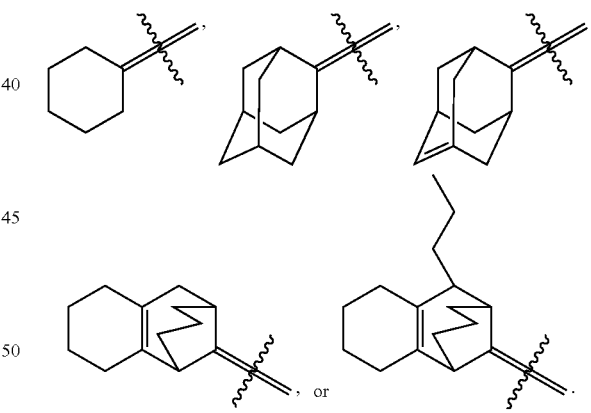

In some embodiments, $R_1$ may be alkyl containing 1 to 2 carbon atoms or trifluoalkyl containing 1 to 2 carbon atoms.

In some embodiments, T may be

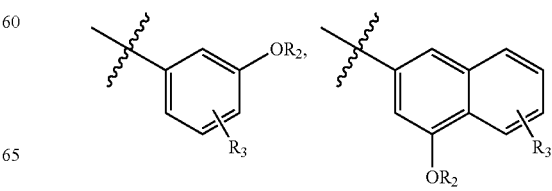

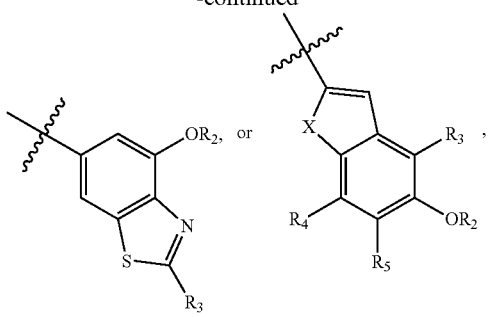

with $R_3$, $R_4$, and $R_5$, independently selected from the group consisting of H, F, Cl, Br, I, cyano, nitro, sulfonate, sulfate, trifluomethyl, trifluoroethyl, straight chain alkyl containing 1 to 20 carbon atoms, branched alkyl containing 3 to 20 carbon atoms, straight chain alkenyl containing 2 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms, polycycloheteroalkenyl containing 4 to 60 carbon atoms, alkoxy containing 1 to 20 carbon atoms, aryl containing 6 to 14 carbon atoms, aryloxy containing 6 to 14 carbon atoms, ester containing 2 to 21 carbon atoms, trialkylammonium containing 3 to 30 carbon atoms, trialkylphosphonium containing 3 to 30 carbon atoms, alkylamido containing 2 to 21 carbon atoms, arylamido containing 7 to 15 carbon atoms, alkylcarbamoyl containing 2 to 21 carbon atoms, arylcarbamoyl containing 7 to 15 carbon atoms, alkylsulfonamido containing 1 to 20 carbon atoms, arylsulfonamido containing 6 to 14 carbon atoms, trialkylsilyl containing 3 to 60 carbon atoms, triarylsilyl containing 18 to 42 carbon atoms, alkylarylsilyl containing 7 to 32 carbon atoms, alkylamidosulfonyl containing 1 to 20 carbon atoms, arylamidosulfonyl containing 6 to 14 carbon atoms, alkylsulfonyl containing 1 to 20 carbon atoms, arylsulfonyl containing 6 to 14 carbon atoms, alkylthio containing 2 to 20 carbon atoms and arylthio containing 6 to 14 carbon atoms, and X is a sulfur atom, oxygen atom, or nitrogen atom.

In some embodiments, $OR_2$ may be phosphate, acetate, 1-phospho-2,3-diacylglyceride, adenosine triphosphate, adenosine diphosphate, adenosine monophosphate, adenosine, α-D-galactoside, β-D-galactoside, α-D-glucoside, β-D-glucoside, α-D-mannoside, β-D-mannoside, β-fructofuranoside, β-D-glucuronide, or

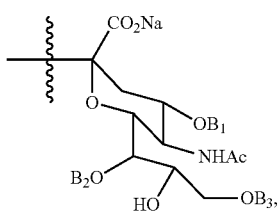

wherein, $B_1$, $B_2$ and $B_3$ are each independently H or an alkyl (branched or straight chain) of 1-4 carbon atoms.

In some embodiments, $R_2$ may be

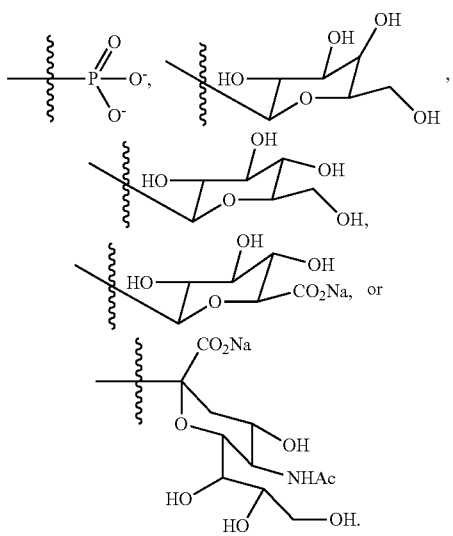

In some embodiments, $R_2$ may be E-L-Nuc-Z, wherein $R_2$ is E-L-Nuc-Z, wherein E is a group comprising an electrophilic atom, which atom upon the enzymatic cleavage of the Z group is attacked by the electron pair of the Nuc group and by anchimeric assistance releases the 1,2-dioxetane enzyme substrate anion; L is a linking group; Nuc is nucleophic atom; and Z is an enzymatically cleavable group; wherein E is carboxyl, carbonyl, methylene substituted by a leaving group, phosphate, carbonate, xanthate, sulfite, sulfonate, bisulfite or bisulfide; L is selected from the group consisting of methylene or polymethylene containing 1 to 4 carbon atoms, —$(CH_2)_m$—O—$(CH_2)_n$—, —$(CH_2)_m$—S—$(CH_2)_n$—, or —$(CH_2)_m$—$NR_6$—$(CH_2)_n$—, wherein m and n are 0 to 3 and m+n is 2 or 3, wherein $R_6$ is alkyl containing 1 to 10 carbon atoms and the linking group may be substituted by alkyl containing 1 to 24 carbon atoms, alkenyl containing 2 to 24 carbon atoms, alkyl containing 1 to 24 carbon atoms and mono- or di-substituted with acyloxy containing 1 to 24 carbon atoms, alkenyl containing 2 to 24 carbon atoms and mono- or disubstituted with acyloxy containing 1 to 24 carbon atoms, aryl containing 6 to 10 carbons, alkyl containing 1 to 24 carbon atoms and substituted with phenyl, hydroxyphenyl, indolyl, mercapto, alkylthio containing 1 to 4 carbon atoms, hydroxy, carboxy, amino, guanidino, imidazole or carbamyl, or alkenyl containing 2 to 24 carbon atoms and substituted with phenyl, hydroxyphenyl, indolyl, mercapto, alkylthio containing 1 to 4 carbon atoms, hydroxy, carboxy, amino, guanidino, imidazole or carbamyl; Nuc is an oxygen atom or sulfur atom; and Z is phosphoryl, acetyl, 1-phospho-2,3-diacylglycerosyl, adenosine triphosphoryl, adenosine diphosphoryl adenosine monophosphoryl, adenosyl, α-D-galactosyl, β-D-galactosyl, α-D-glucosyl, β-D-glucosyl, α-D-mannosyl, β-D-mannosyl, β-fructofuranosyl, β-D-glucosiduransyl or

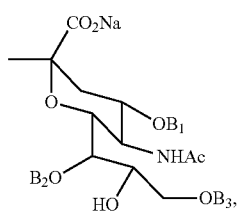

wherein, $B_1$, $B_2$ and $B_3$ are each independently H or an alkyl (branched or straight chain) of 1-4 carbon atoms. In some of these, Z is

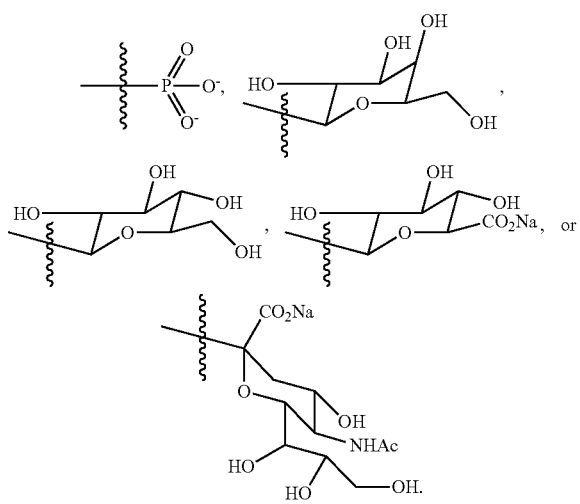

The enzyme moiety may comprise a hydrolytic enzyme. In some embodiments, the hydrolytic enzyme may be alkaline phosphatase, β-galactosidase, β-glucosidase, β-glucuronidase or neuraminidase.

In some embodiments, the enzyme moiety may be an enzyme.

In some embodiments, the methods may further comprise the step of detecting any light emitted from the reaction mixture after addition of the aqueous solution of the 1,2-dioxetane enzyme substrate, wherein the emission of light is indicative of the presence of the enzyme, and the amount of light emitted can be correlated to the amount of the enzyme present in the sample.

In some embodiments, the enzyme moiety may be an enzyme-linked antibody comprising a first antibody capable of binding to the antigen and an enzyme capable of cleaving the 1,2-dioxetane enzyme substrate so that the substrate decomposes and generates light.

In some of embodiments, the first antibody may be covalently or non-covalently linked to the enzyme. In some of these, the first antibody may be covalently linked to a label and the enzyme may be covalently linked to a molecule capable of non-covalently binding to the label. In some of these, the label may be biotin, or a biotin derivative, and the molecule may be avidin or strepavidin. In others, the label may be a hapten and the molecule may be an antibody capable of binding to the hapten.

In some embodiments, the methods may further comprise the steps of (a) providing a sample suspected of comprising an antigen; (b) providing a solid phase comprising a second antibody capable of binding to the antigen; (c) contacting the sample and enzyme-linked antibody with the solid phase to form an enzyme complex; and, (d) detecting the light emitted from the reaction mixture after addition of the aqueous solution of the 1,2-dioxetane enzyme substrate, wherein the emission of light is indicative of the presence of the antigen, and the amount of light emitted can be correlated to the amount of the antigen present in the sample.

In some embodiments, the methods may further comprise the step of removing any unbound enzyme-linked antibody from the enzyme complex.

In some embodiments, the enzyme moiety may be an enzyme-linked antigen comprising an antigen and an enzyme capable of cleaving the 1,2-dioxetane enzyme substrate so that the substrate decomposes and generates light.

In some embodiments, the antigen may be covalently or noncovalently linked to the enzyme.

In some embodiments, the antigen may be covalently linked to a label and the enzyme may be covalently linked to a molecule capable of non-covalent binding to the label. In some of these, the label may be biotin, or a biotin derivative, and the molecule may be avidin or strepavidin. In others, the label may be a hapten and the molecule may be an antibody capable of binding to the hapten.

In some embodiments, the methods may further comprise the steps of (a) providing a sample suspected of comprising an antigen; (b) providing a solid phase comprising an antibody capable of binding to the antigen; (c) contacting the sample and enzyme-linked antigen with the solid phase to form an enzyme complex; and, (d) detecting the light emitted from the reaction mixture after addition of the aqueous solution of the 1,2-dioxetane enzyme substrate, wherein the amount of light emitted can be correlated to the amount of the antigen present in the sample.

In some embodiments, the methods may further comprise the step of removing any unbound enzyme-linked antigen from the enzyme complex.

In some embodiments, the enzyme moiety may be an enzyme-linked oligonucleotide comprising an oligonucleotide capable of hybridizing to a nucleic acid and an enzyme capable of cleaving the 1,2-dioxetane enzyme substrate so that the substrate decomposes and generates light.

In some embodiments, the oligonucleotide may be covalently or non-covalently linked to the enzyme.

In some embodiments, the oligonucleotide may be covalently linked to a label and the enzyme may be covalently linked to a molecule capable of non-covalent binding to the label. In some of these, the label may be biotin, or a biotin derivative, and the molecule may be avidin or strepavidin. In others, the label may be a hapten and the molecule may be an antibody capable of binding to the hapten.

In some embodiments, the methods may further comprise the steps of (a) providing a sample suspected of comprising a nucleic acid; (b) immobilizing the nucleic acid to a solid phase, (c) contacting the immobilized nucleic acid and the enzyme-linked oligonucleotide to form an enzyme complex; and (d) detecting the light emitted from the reaction mixture after addition of the aqueous solution of the 1,2-dioxetane enzyme substrate, wherein the emission of light is indicative of the presence of the nucleic acid, and the amount of light emitted can be correlated to the amount of the nucleic acid present in the sample.

In some embodiments, the methods may further comprise the step of removing any unbound enzyme-linked oligonucleotide from the enzyme complex.

In some embodiments, the reaction mixture may further comprise an enhancer.

In some embodiments, the enhancer may comprise a polymeric quaternary ammonium salt, polymeric quaternary phosphonium salt, or a combination thereof. In some of these, the enhancer may further comprise an acceptor dye. Among some of these, the acceptor dye may be fluorescein.

In some embodiments, the polymeric quaternary ammonium salt may be poly(vinylbenzyltrimethylammonium chloride), poly[vinylbenzyl(benzyldimethylammonium chloride)], poly[vinyl(benzyltributylammonium chloride)], poly[vinyl(benzyltripentylammonium chloride)] or a combination thereof.

In other embodiments, the polymeric quaternary phosphonium salt may be poly(vinylbenzyltrimethylphosphonium chloride), poly(vinylbenzyltributylphosphonium chloride), poly(vinylbenzyltrioctylphosphonium chloride), a copolymer comprising poly(vinylbenzyltributylphosphonium chloride) and poly(vinylbenzyltrioctylphosphonium chloride), or a combination thereof.

In some embodiments, the enol ether [1] may be

[2]
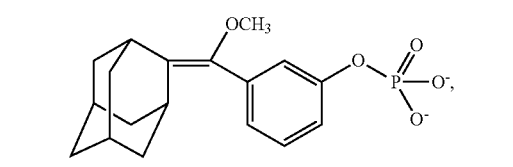

[3]
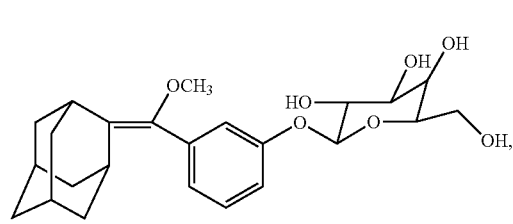

[4]
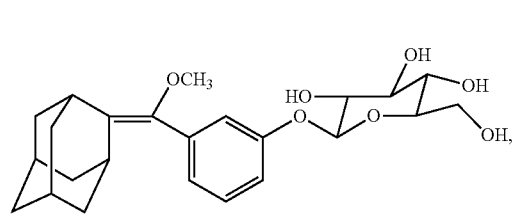

[5]
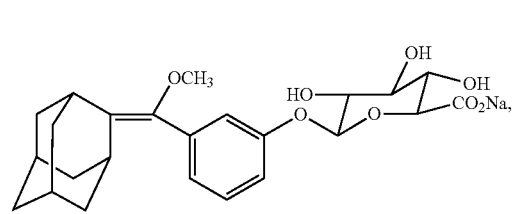

[6]
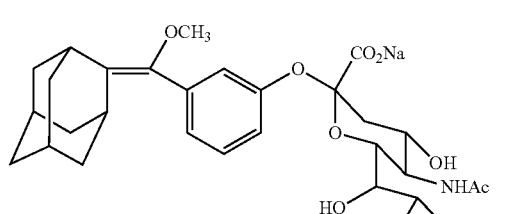

[7]
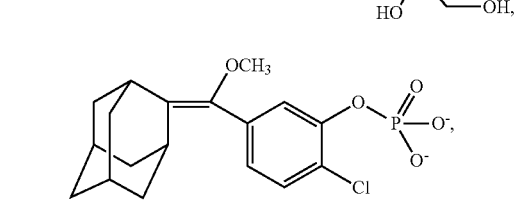

[8]
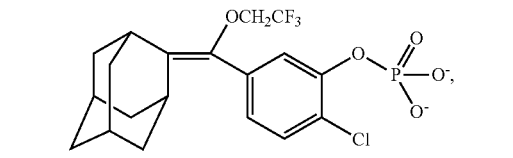

-continued

[9]
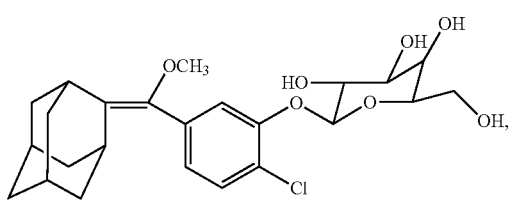

[10]
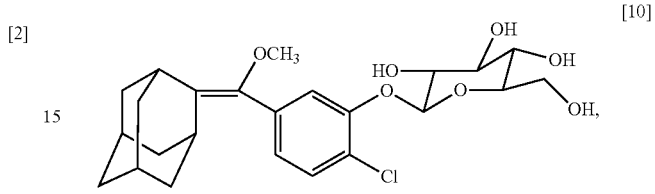

[11]
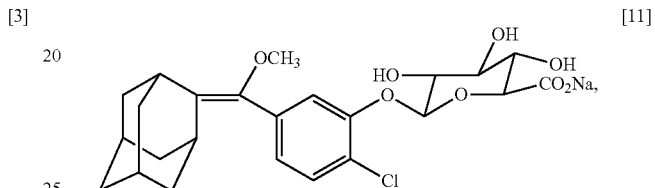

[12]
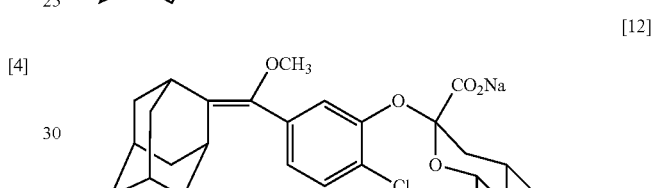

[13]
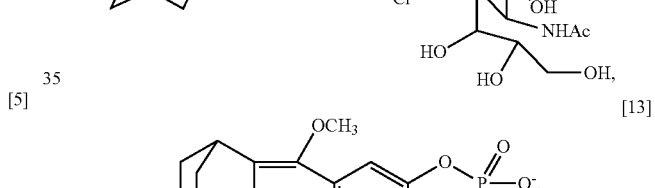

[14]
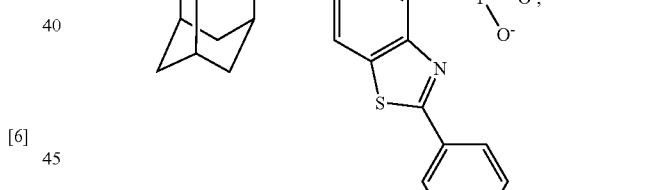

[15]
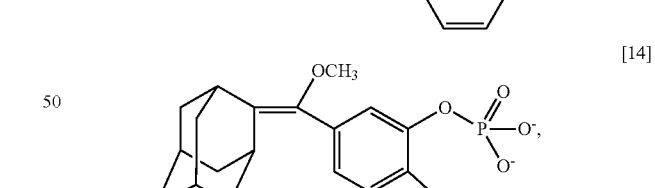

-continued

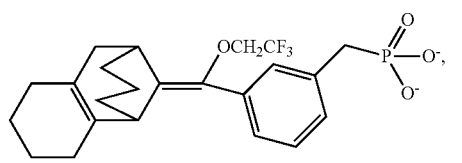
[16]

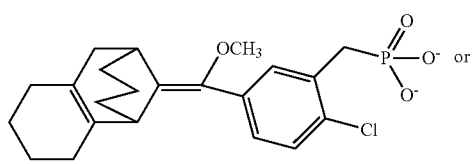
[17]

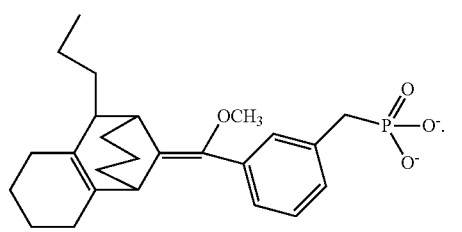
[18]

In another aspect, the present invention provides assay methods for determining the presence or amount of an enzyme in a sample, comprising the steps of: (a) providing an oxidant; (b) providing an enol ether having the structure [1] and having the substituents as described above; (c) combining an aqueous solution, the oxidant, and the enol ether to form an aqueous solution comprising a 1,2-dioxetane enzyme substrate; (d) providing a sample suspected of comprising the enzyme which is capable of cleaving the 1,2-dioxetane enzyme substrate so that the substrate decomposes and generates light; (e) contacting the sample with the aqueous solution comprising the 1,2-dioxetane enzyme substrate to form a reaction mixture; and, (f) detecting the light emitted from the reaction mixture after addition of the aqueous solution of the 1,2-dioxetane enzyme substrate, wherein the emission of light is indicative of the presence of the enzyme, and the amount of light emitted can be correlated to the amount of the enzyme present in the sample.

In another aspect, the present invention provides assay methods for determining the presence or amount of an antigen in a sample, comprising the steps of: (a) providing an oxidant; (b) providing an enol ether having the structure [1] and having the substituents as described above; (c) combining an aqueous solution, the oxidant, and the enol ether to form an aqueous solution comprising a 1,2-dioxetane enzyme substrate; (d) providing a sample suspected of comprising the antigen; (e) providing an enzyme-linked antibody comprising a first antibody capable of binding to the antigen and an enzyme capable of cleaving the 1,2-dioxetane enzyme substrate so that the substrate decomposes and generates light; (f) providing a solid phase comprising a second antibody capable of binding to the antigen; (g) contacting the sample and enzyme-linked antibody with the solid phase to form an enzyme complex; (h) contacting the enzyme complex with the aqueous solution comprising the 1,2-dioxetane enzyme substrate to form a reaction mixture; and, (i) detecting the light emitted from the reaction mixture after addition of the aqueous solution of the 1,2-dioxetane enzyme substrate, wherein the emission of light is indicative of the presence of the antigen, and the amount of light emitted can be correlated to the amount of the antigen present in the sample.

In another aspect, the present invention provides assay methods for determining the presence or amount of an antigen in a sample, comprising the steps of: (a) providing an oxidant; (b) providing an enol ether having the structure [1] and having the substituents as described above; (c) combining an aqueous solution, the oxidant and the enol ether to form an aqueous solution comprising a 1,2-dioxetane enzyme substrate; (d) providing a sample suspected of comprising the antigen; (e) providing an enzyme-linked antigen comprising the antigen and an enzyme capable of cleaving the 1,2-dioxetane enzyme substrate so that the substrate decomposes and generates light; (f) providing a solid phase comprising an antibody capable of binding to the antigen; (g) contacting the sample and enzyme-linked antigen with the solid phase to form an enzyme complex; (h) contacting the enzyme complex with the aqueous solution comprising the 1,2-dioxetane enzyme substrate to form a reaction mixture; and, (i) detecting the light emitted from the reaction mixture after addition of the aqueous solution of the 1,2-dioxetane enzyme substrate, wherein the amount of light emitted can be correlated to the amount of the antigen present in the sample.

In another aspect, the present invention provides assay methods for determining the presence or amount of a nucleic acid in a sample, comprising the steps of (a) providing an oxidant; (b) providing an enol ether having the structure [1] and having the substituents as described above; (c) combining an aqueous solution, the oxidant, and the enol ether to form an aqueous solution comprising a 1,2-dioxetane enzyme substrate; (d) providing a sample suspected of comprising the nucleic acid; (e) immobilizing the nucleic acid to a solid phase; (f) providing an enzyme-linked oligonucleotide comprising an oligonucleotide capable of hydridizing to the nucleic acid and an enzyme capable of cleaving the 1,2-dioxetane enzyme substrate so that the substrate decomposes and generates light; (g) contacting the immobilized and enzyme-linked oligonucleotide to form an enzyme complex; (h) contacting the enzyme complex with the aqueous solution comprising the 1,2-dioxetane enzyme substrate to form a reaction mixture; and, (i) detecting the light emitted from the reaction mixture after addition of the aqueous solution of the 1,2-dioxetane enzyme substrate, wherein the emission of light is indicative of the presence of the nucleic acid, and the amount of light emitted can be correlated to the amount of the nucleic acid present in the sample.

In another aspect, the present invention provides kits for detecting the presence and/or amount of an analyte in a sample. The kits include an oxidant, and an enol ether having the structure [1] and having the substituents as described above. The various embodiments of the enol ether have the structure [1] and its substituents, and the oxidant, also are described above and are equally applicable to the kits and methods of the present invention.

In some embodiments, the kits may further comprise an enhancer.

In some embodiments, the enhancer may comprise a polymeric quaternary ammonium salt, polymeric quaternary phosphonium salt, or a combination thereof. In some of these, the enhancer may further comprise an acceptor dye. In some of these, the acceptor dye may be fluorescein.

In some embodiments, the polymeric quaternary ammonium salt may be poly(vinylbenzyltrimethylammonium chloride), poly[vinylbenzyl(benzyldimethylammonium chloride)], poly[vinyl(benzyltributylammonium chloride)], poly[vinyl(benzyltripentylammonium chloride)], or a combination thereof.

In other embodiments, the polymeric quaternary phosphonium salt may be poly(vinylbenzyltrimethylphosphonium chloride), poly(vinylbenzyltributylphosphonium chloride), poly(vinylbenzyltrioctylphosphonium chloride), a copolymer comprising poly(vinylbenzyltributylphosphonium chloride) and poly(vinylbenzyltrioctylphosphonium chloride), or a combinations thereof.

In some embodiments, the enol ether having the structure [1] may be any one of the enol ethers, [2] through [18], as shown above.

In another aspect, the present invention provides a method for making a 1,2-dioxetane enzyme substrate, comprising the steps of (a) providing an oxidant; (b) providing an enol ether having the structure:

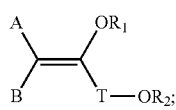

[1]

and
(c) combining an aqueous solution, the oxidant, and the enol ether to form an aqueous solution comprising a 1,2-dioxetane enzyme substrate.

DETAILED DESCRIPTION OF THE INVENTION

Figure 1:
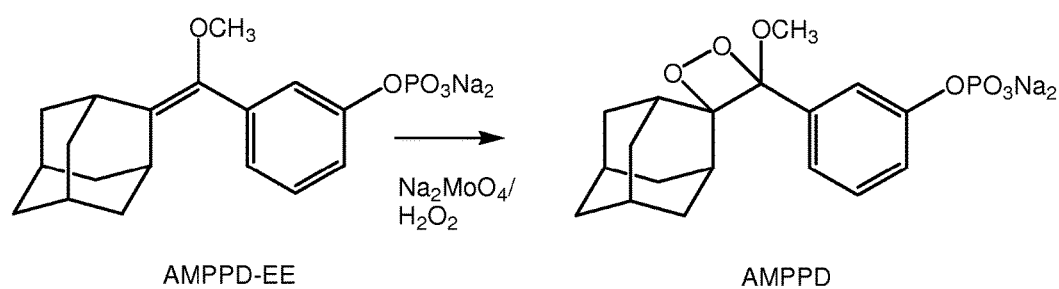
FIG. 1 shows the reaction scheme for the conversion of AMPPD enol ether phosphate (AMPPD-EE) to the dioxetane substrate, AMPPD®, in an aqueous solution using the oxidation system of $Na_2MoO_4/H_2O_2$ at alkaline pH.

Before describing the present invention in detail, it is to be understood that this invention is not limited to the embodiments disclosed herein. Further, while the methods and kits are described in terms of "comprising" various steps or components (interpreted as meaning, "including, but not limited to"), the methods and kits can also "consist essentially of" or "consist of" the various steps and components, such terminology should be interpreted as defining essentially closed-member groups. Finally, it is be noted that, as used in this specification and the appended claims, the singular form "a", "an" and "the" include plural referents unless the context clearly dictates otherwise.

Definitions

Acceptor dye refers to a molecule which can accept energy, especially light, from another light-emitting molecule and in turn emit detectable energy, again preferably light.

Analyte refers to a substance or chemical constituent that is determined in an analytical procedure. As used herein, the term includes, but is not limited to, an antigen or antibody.

Antigen refers to a substance to which an antibody can bind.

Antibody refers to gamma globulin proteins that are found in blood or other bodily fluids of vertebrates, and are used by the immune system to identify and neutralize foreign objects. As used herein, the term includes, but is not limited to, any polyclonal, monoclonal, recombinant antibody or fragments thereof which can bind an antigen.

Enhancer refers to a water-soluble substance that increases specific light energy production resulting from the enzymatic cleavage of a 1,2-dioxetane enzyme substrate and its subsequent decomposition, where this light production observed is above that observed in the absence of the enhancer.

Enzyme refers to proteins that catalyze chemical reactions.

Hapten refers to a small molecule that can elicit an immune response only when attached to a large carrier such as a protein.

Hydrolytic enzyme or hydrolase refers to an enzyme that catalyzes the hydrolysis of a chemical bond and would be classified as EC 3 in the EC number classification of enzymes.

Nucleic acid refers DNA, RNA or fragment thereof.

Oligonucleotide refers to a short nucleic acid polymer. As used here, the term includes, but is not limited to, a nucleic acid polymer comprising 2 to 1000 nucleic acids.

Oxidant is a chemical compound that readily transfers oxygen atoms, or a substance that gains electrons in a redox chemical reaction. As used herein, term is used interchangeably with terms, oxidizing agent or oxidizer.

The present invention provides methods for generating a chemiluminescent enzyme substrate in situ in aqueous or other conditions, and/or using this substrate to generate light. The generation of light can be used to determine the presence in a sample of an enzyme, antigen or a nucleic acid. These methods relate to a stabilized enol ether and an oxidant, which when combined form in an aqueous solution a 1,2-dioxetane enzyme substrate. The present invention also provides kits for detection of the presence and/or amount of an analyte in a sample. The kits comprise a stabilized enol ether and an oxidant, which when combined form in an aqueous solution a 1,2-dioxetane enzyme substrate. These methods, as well as the kits, have utility in art-recognized assays.

Viewed from one aspect, the present invention provides methods for generating light. The methods comprise the steps of providing an oxidant; providing an enol ether having the structure shown below:

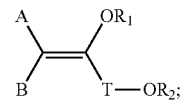

combining an aqueous solution, the oxidant, and the enol ether to form an aqueous solution comprising a 1,2-dioxetane enzyme substrate; providing an enzyme complex comprising an enzyme moiety which is capable of cleaving the 1,2-dioxetane enzyme substrate; contacting the enzyme complex with the aqueous solution comprising the 1,2-dioxetane enzyme substrate to form a reaction mixture; and allowing the reaction mixture to generate light.

In one step of these methods, an oxidant is provided. This oxidant would be one that can convert the enol ether [1] to its corresponding 1,2-dioxetane enzyme substrate.

In some embodiments, the oxidant may be selected from hydrogen peroxide, sodium molybdate, hydrogen peroxide and sodium molybdate, hypochlorite, hypochlorite and hydrogen peroxide, aryl endoperoxide, calcium peroxide peroxyhydrate, and combinations thereof. In some of these embodiments, the oxidant may be hydrogen peroxide, or hydrogen peroxide and sodium molybdate.

The oxidant may be provided as a solution or as a powder. Where the oxidant comprises multiple components, one or more, but not all, of these components may be combined with or without the enol ether.

In another step of these methods, an enol ether [1] is provided.

In some embodiments, the enol ether [1] may have an A and B which are independently selected from the group consisting of straight chain alkyl, straight chain alkenyl, branched alkyl, branched alkenyl, cycloalkyl, cycloalkenyl, cycloheteroalkyl, cycloheteroalkenyl, polycycloalkyl, polycycloalkenyl, polycycloheteroalkyl and polycycloheteroalkenyl, any of which can be unsubstituted or substituted with one or more electron-active groups, solubilizing groups, or light-enhancing groups, and where A and B together form the cycloalkyl, cycloalkenyl, polycycloalkyl or polycycloalkenyl, one of the carbon atoms of the cycloalkyl, cycloalkenyl, polycycloalkyl or polycycloalkenyl is one of two carbon atoms forming the double bond of the enol ether.

Examples of electron-active groups include: F, Cl, Br, I, cyano, nitro, sulfonate, sulfate, trifluoromethyl, trifluoroethyl, straight chain alkyl containing 1 to 20 carbon atoms, branched alkyl containing 3 to 20 carbon atoms, straight chain alkenyl containing 2 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms, polycycloheteroalkenyl containing 4 to 60 carbon atoms, alkoxy containing 1 to 20 carbon atoms, aryl containing 6 to 14 carbon atoms, aryloxy containing 6 to 14 carbon atoms, ester containing 2 to 21 carbon atoms, trialkylammonium containing 3 to 30 carbon atoms, trialkylphosphonium containing 3 to 30 carbon atoms, alkylamido containing 2 to 21 carbon atoms, arylamido containing 7 to 15 carbon atoms, alkylcarbamoyl containing 2 to 21 carbon atoms, arylcarbamoyl containing 7 to 15 carbon atoms, alkylsulfonamido containing 1 to 20 carbon atoms, arylsulfonamido containing 6 to 14 carbon atoms, trialkylsilyl containing 3 to 60 carbon atoms, triarylsilyl containing 18 to 42 carbon atoms, alkylarylsilyl containing 7 to 32 carbon atoms, alkylamidosulfonyl containing 1 to 20 carbons, arylamidosulfonyl containing 6 to 14 carbon atoms, alkylsulfonyl containing 1 to 20 carbon atoms, arylsulfonyl containing 6 to 14 carbon atoms, alkylthio containing 2 to 20 carbon atoms and arylthio containing 6 to 14 carbon atoms.

Examples of solubilizing groups include: carboxylic acids, malonic acid, hydroxyls, sulfates, sulfonates, phosphates, and ammonium groups; poly(ethoxy)$_n$ groups [—(O—CH$_2$—CH$_2$—)$_n$], where n=1-30, terminated by carboxylic acids, malonic acid, hydroxyls, sulfates, sulfonates, phosphates, and ammonium groups; poly[-O—(CH$_2$—)$_n$], where n=1-30, terminated by carboxylic acids, malonic acid, hydroxyls, sulfates, sulfonates, phosphates, and ammonium groups.

Examples of light enhancing groups include: cationic or polycationic moieties such as alkylammonium, alkylphosphonium, alkylsulfonium groups; alkylarylammonium, alkylarylphosphonium, and alkylaryl sulfonium groups; or arylammonium, arylphosphonium and arylsulfonium groups; and poly(alkylammonium), poly(alkylphosphonium), poly(alkylsulfonium) groups; poly(alkylarylammonium), poly(alkylarylphosphonium), and polyalkylaryl sulfonium groups; or poly(arylammonium), poly(arylphosphonium) and poly(arylsulfonium) groups.

In some embodiments, A and B may be independently selected from the group consisting of straight chain alkyl containing 1 to 20 carbon atoms, straight chain alkenyl containing 2 to 20 carbon atoms, branched alkyl containing 3 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms and polycycloheteroalkenyl containing 4 to 60 carbon atoms, any of which can be unsubstituted or substituted with one or more electron-active groups, solubilizing groups, or light-enhancing groups, and where A and B together form the cycloalkyl, cycloalkenyl, polycycloalkyl or polycycloalkenyl, one of the carbon atoms of the cycloalkyl, cycloalkenyl, polycycloalkyl or polycycloalkenyl is one of two carbon atoms forming the double bond of the enol ether.

In some embodiments, at least one of A or B may be

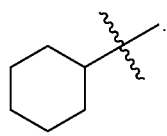 [SMILES: *C1CCCCC1]

In other embodiments, A and B together may be

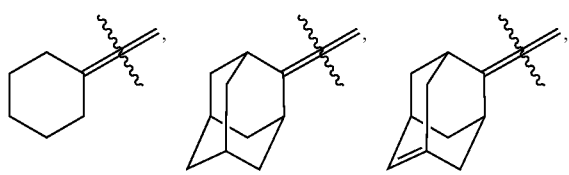

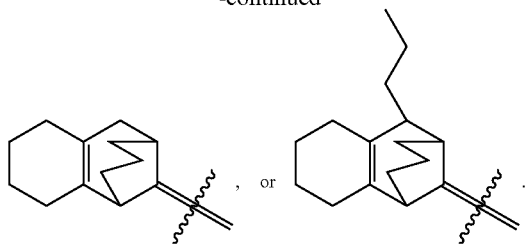

In some embodiments, the enol ether [1] will have an R$_1$ which may be an alkyl, aryl, aralkyl, heteroaryl, or heteroaralkyl. In some of these, R$_1$ may be an alkyl containing 1 to 20 carbon atoms, aryl containing 6 to 14 carbon atoms, aralkyl containing 7 to 15 carbon atoms, heteroaryl containing 4 to 20 carbon atoms, or heteroaralkyl containing 5 to 20 carbons. In some these, R$_1$ may be an alkyl containing 1 to 2 carbon atoms or trifluoalkyl containing 1 to 2 carbon atoms.

In some embodiments, the enol ether [1] will have a T which may be an aryl or fused polycyclic ring compound which includes, but is not limited to, a heteroaryl ring, which is capable of emitting light. T is chosen so that it does not interfere with the production of light and satisfies the valence of the 4-carbon atom of the dioxetane ring to which it is attached. T represents any of a number of light-emitting fluorophore-forming fluorescent chromophore groups that permit the corresponding dioxetane decomposition fragments to absorb energy and form an excited state from which they emit optically detectable energy to return to their ground state. T is also substituted with an enzyme cleavable group that contains a bond cleavable by an enzyme to yield either directly or by subsequent adjustment of pH an electron-rich moiety, for example, an oxygen anion, a sulfur anion or a nitrogen anion, bonded to the dioxetane ring.

In some embodiments, T may be an aryl, such as phenyl, which may be substituted with electron-active groups, solubilizing groups or light-enhancing groups.

In some embodiments, T may a fused polycyclic ring-containing fluorophore moiety having an enzymatically cleavable labile ring substituent containing a bond which, when cleaved by an enzyme, renders the fused polycyclic moiety electron-rich to in turn render the dioxetane compound decomposable to emit light.

Included among the fused polycyclic ring compounds whose residues can be used to form this fluorophore moiety are fused polycyclic aromatic hydrocarbon ring fluorophoric compounds containing from 9 to about 30 ring carbon atoms, inclusive, such as naphthalene:

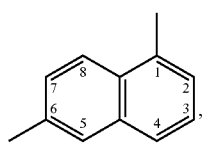

pentalene, azulene, heptalene, asindacene, s-indacene, biphenylene, perylene, acenaphthylene, phenanthrene, anthracene, acephenanthrylene, aceanthrylene, triphenylene, pyrene, chrysene, naphthacene, and the like, as well as derivatives thereof substituted with one or more non-labile substituents such as a branched or straight chain alkyl group having 1 to 20 carbon atoms, inclusive, e.g., methyl, n-butyl or decyl, a branched or straight chain heteroalkyl group having 1 to 7 carbon atoms, inclusive, e.g., methoxy, hydroxyethyl or hydroxypropyl; an aryl group having 1 or 2 rings, e.g., phenyl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; an alkaryl group having 1 or 2 rings, e.g., tolyl; an electron-withdrawing group, such as a per-fluoroalkyl group having between 1 and 7 carbon atoms, inclusive, e.g., trifluoromethyl; a halogen; $CO_2H$, $ZCO_2H$, $SO_3H$, $NO_2$, $ZNO_2$, CN, or ZCN, where Z is a branched or straight chain alkyl group having 1 to 7 carbon atoms, inclusive, e.g., methyl, or an aryl group having 1 or 2 rings, e.g., phenyl; an electron-donating group, e.g., a branched or straight chain $C_1$-$C_7$ alkoxy group, e.g., methoxy or ethoxy: an aralkoxy group having 1 or 2 rings, e.g., phenoxy; a branched or straight chain $C_1$-$C_7$ alkoxy group, e.g., methoxy or ethoxy; an aralkoxy group having 1 or 2 rings, e.g., phenoxy; a branched or straight chain $C_1$-$C_7$ hydroxy-alkyl group, e.g., hydroxymethyl or hydroxyethyl; a hydroxyaryl group having 1 or 2 rings, e.g., hydroxyphenyl; a branched or straight chain $C_1$-$C_7$ alkyl ester group, e.g., acetate; an aryl ester group having 1 or 2 rings, e.g., benzoate; or a heteroaryl group having 1 or 2 rings, e.g., benzoxazole, benzthiazole, benzimidazole or benztriazole.

Further, the fused polycyclic ring portion of the fluorophore moiety represented by T can also be the residue of a fused polycyclic aromatic heterocyclic ring fluorophoric compound, e.g., benzo[b]thiophene, naphtho[2,3-b]thiophene, thianthrene, benzofuran, isobenzofuran, chromene, xanthene, phenoxathine, quinoline, isoquinoline, phenanthridine, phenazine, phenoxazine, phenothiazine, phenanthroline, purine, 4H-quinolizine, phthalazine, naphthyridine, indole, indolizine, chroman, isochroman, indoline, isoindoline, and the like, unsubstituted or substituted with one or more of the aforementioned non-labile substituents, and containing from 9 to about 30 ring atoms, inclusive, the bulk of which are carbon atoms.

In some embodiments, T may be

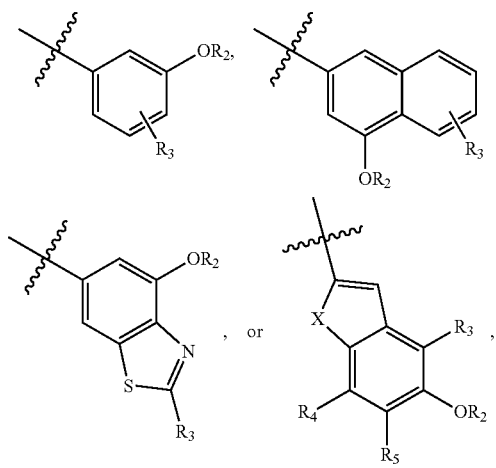

wherein $R_3$, $R_4$, and $R_5$, are independently selected from the group consisting of H, F, Cl, Br, I, cyano, nitro, sulfonate, sulfate, trifluomethyl, trifluoroethyl, straight chain alkyl, branched alkyl, straight chain alkenyl, branched alkenyl, cycloalkyl, cycloalkenyl, cycloheteroalkyl, cycloheteroalkenyl, polycycloalkyl, polycycloalkenyl, polycycloheteroalkyl, polycycloheteroalkenyl, alkoxy, aryl, aryloxy, ester, trialkylammonium, trialkylphosphonium, alkylamido, arylamido, alkylcarbamoyl, arylcarbamoyl, alkylsulfonamido, arylsulfonamido, trialkylsilyl, triarylsilyl, alkylarylsilyl, alkylamidosulfonyl, arylamidosulfonyl, alkylsulfonyl, arylsulfonyl, alkylthio and arylthio. In some of these, $R_3$, $R_4$, and $R_5$, may be independently selected from the group consisting of H, F, Cl, Br, I, cyano, nitro, sulfonate, sulfate, trifluomethyl, trifluoroethyl, straight chain alkyl containing 1 to 20 carbon atoms, branched alkyl containing 3 to 20 carbon atoms, straight chain alkenyl containing 2 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms, polycycloheteroalkenyl containing 4 to 60 carbon atoms, alkoxy containing 1 to 20 carbon atoms, aryl containing 6 to 14 carbon atoms, aryloxy containing 6 to 14 carbon atoms, ester containing 2 to 21 carbon atoms, trialkylammonium containing 3 to 30 carbon atoms, trialkylphosphonium containing 3 to 30 carbon atoms, alkylamido containing 2 to 21 carbon atoms, arylamido containing 7 to 15 carbon atoms, alkylcarbamoyl containing 2 to 21 carbon atoms, arylcarbamoyl containing 7 to 15 carbon atoms, alkylsulfonamido containing 1 to 20 carbon atoms, arylsulfonamido containing 6 to 14 carbon atoms, trialkylsilyl containing 3 to 60 carbon atoms, triarylsilyl containing 18 to 42 carbon atoms, alkylarylsilyl containing 7 to 32 carbon atoms, alkylamidosulfonyl containing 1 to 20 carbon atoms, arylamidosulfonyl containing 6 to 14 carbon atoms, alkylsulfonyl containing 1 to 20 carbon atoms, arylsulfonyl containing 6 to 14 carbon atoms, alkylthio containing 2 to 20 carbon atoms and arylthio containing 6 to 14 carbon atoms.

In some embodiments, the enol ether [1] may have an $OR_2$ that is phosphate, acetate, 1-phospho-2,3-diacylglyceride, adenosine triphosphate, adenosine diphosphate, adenosine monophosphate, adenosine, α-D-galactoside, β-D-galactoside, α-D-glucoside, β-D-glucoside, α-D-mannoside, β-D-mannoside, β-fructofuranoside, β-D-glucuronide, or

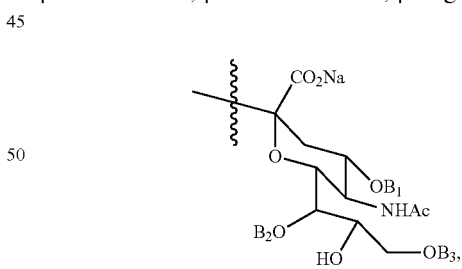

wherein, $B_1$, $B_2$ and $B_3$ are each independently H or an alkyl (branched or straight chain) of 1-4 carbon atoms. In some of these, $R_2$ is

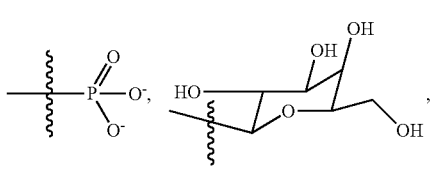

-continued

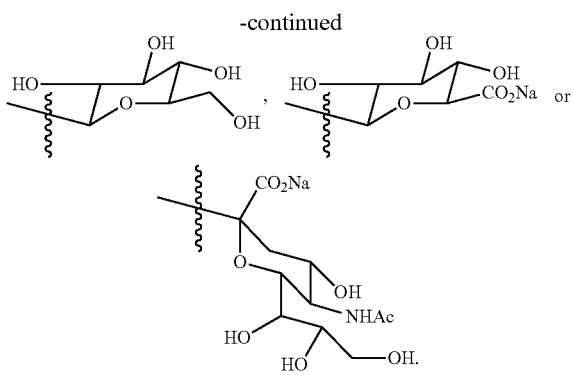

$R_2$, the enzymatically cleavable substituent, may include phosphate ester groups represented by the general formula:

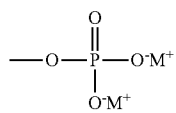

wherein M+ represents a cation such as alkali metal, e.g., sodium or potassium, ammonium, or a $C_{1-7}$ alkyl, aralkyl or aromatic quaternary ammonium cation, $N(DR_3)_4+$ in which each $D_3$ can be alkyl, e.g., methyl or ethyl, aralkyl, e.g., benzyl, or form part of a heterocyclic ring system, e.g., pyridinium, and particularly the disodium salt. Such quaternary ammonium cations can also be connected through one of their quaternizing groups to a polymeric backbone, viz.

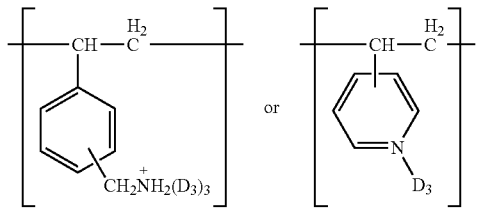

where n is greater than 1, or can be part of a polyquaternary ammonium salt, i.e., an ionene polymer.

In some embodiments, $R_2$ may be E-L-Nuc-Z, wherein E is a group comprising an electrophilic atom, which atom upon the enzymatic cleavage of the Z group is attacked by the electron pair of the Nuc group and by anchimeric assistance releases the 1,2-dioxetane enzyme substrate anion; L is a linking group; Nuc is nucleophic atom; and Z is an enzymatically cleavable group; wherein E may be carboxyl, carbonyl, methylene substituted by a leaving group, phosphate, carbonate, xanthate, sulfite, sulfonate, bisulfite or bisulfide;

L may be selected from the group consisting of methylene or polymethylene containing 1 to 4 carbon atoms, $-(CH_2)_m-O-(CH_2)_n-$, $-(CH_2)_m-S-(CH_2)_n-$, or $-(CH_2)_m-NR_6-(CH_2)_n-$, wherein m and n are 0 to 3 and m+n is 2 or 3, wherein $R_6$ is alkyl containing 1 to 10 carbon atoms and the linking group may be substituted by alkyl containing 1 to 24 carbon atoms, alkenyl containing 2 to 24 carbon atoms, alkyl containing 1 to 24 carbon atoms and mono- or di-substituted with acyloxy containing 1 to 24 carbon atoms, alkenyl containing 2 to 24 carbon atoms and mono- or disubstituted with acyloxy containing 1 to 24 carbon atoms, aryl containing 6 to 10 carbons, alkyl containing 1 to 24 carbon atoms and substituted with phenyl, hydroxyphenyl, indolyl, mercapto, alkylthio containing 1 to 4 carbon atoms, hydroxy, carboxy, amino, guanidino, imidazole or carbamyl, or alkenyl containing 2 to 24 carbon atoms and substituted with phenyl, hydroxyphenyl, indolyl, mercapto, alkylthio containing 1 to 4 carbon atoms, hydroxy, carboxy, amino, guanidino, imidazole or carbamyl;

Nuc may be an oxygen atom or sulfur atom; and

Z may be phosphoryl, acetyl, 1-phospho-2,3-diacylglycerosyl, adenosine triphosphoryl, adenosine diphosphoryl adenosine monophosphoryl, adenosyl, α-D-galactosyl, β-D-galactosyl, α-D-glucosyl, β-D-glucosyl, α-D-mannosyl, β-D-mannosyl, β-fructofuranosyl, β-D-glucosiduransyl, or

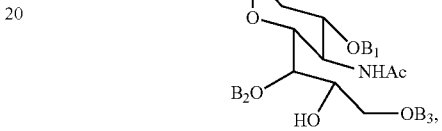

wherein, $B_1$, $B_2$ and $B_3$ are each independently H or an alkyl (branched or straight chain) of 1-4 carbon atoms.

In some embodiments, Z may be

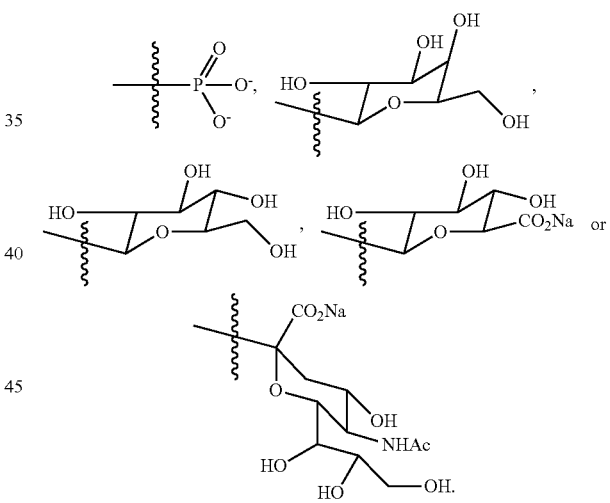

In some embodiments, the enol ether [1] may be

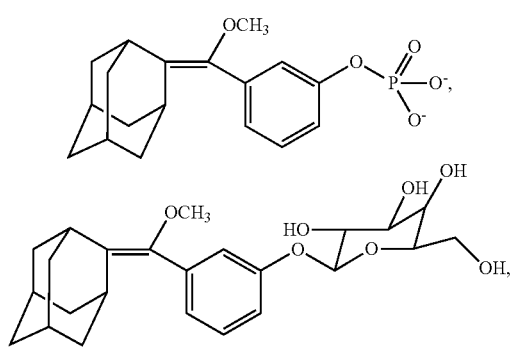

21
-continued

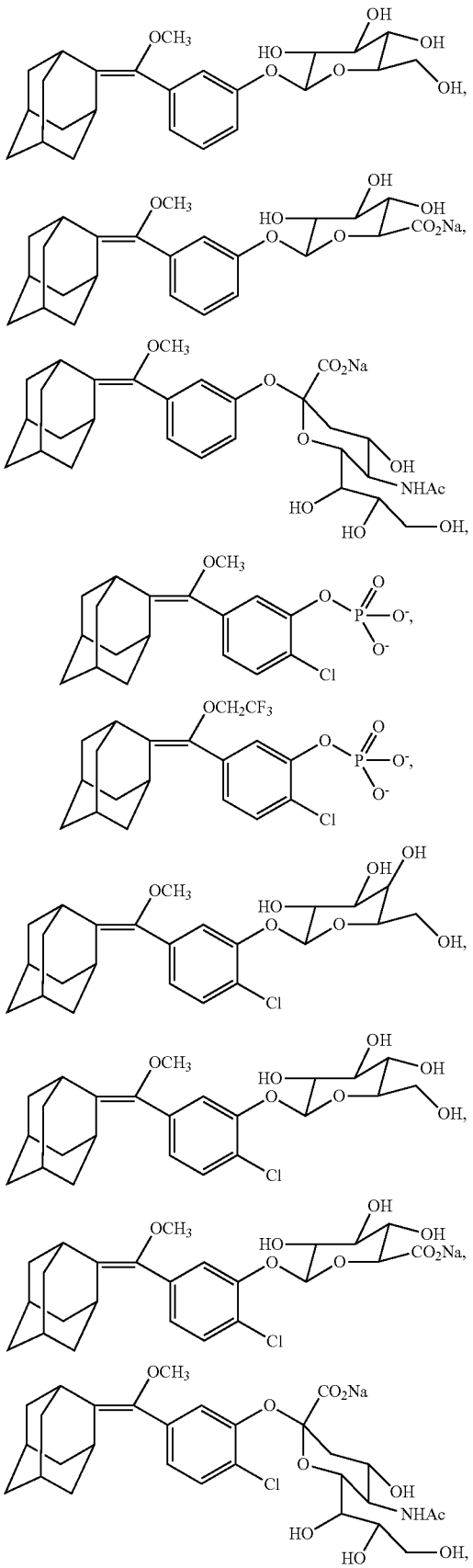

22
-continued

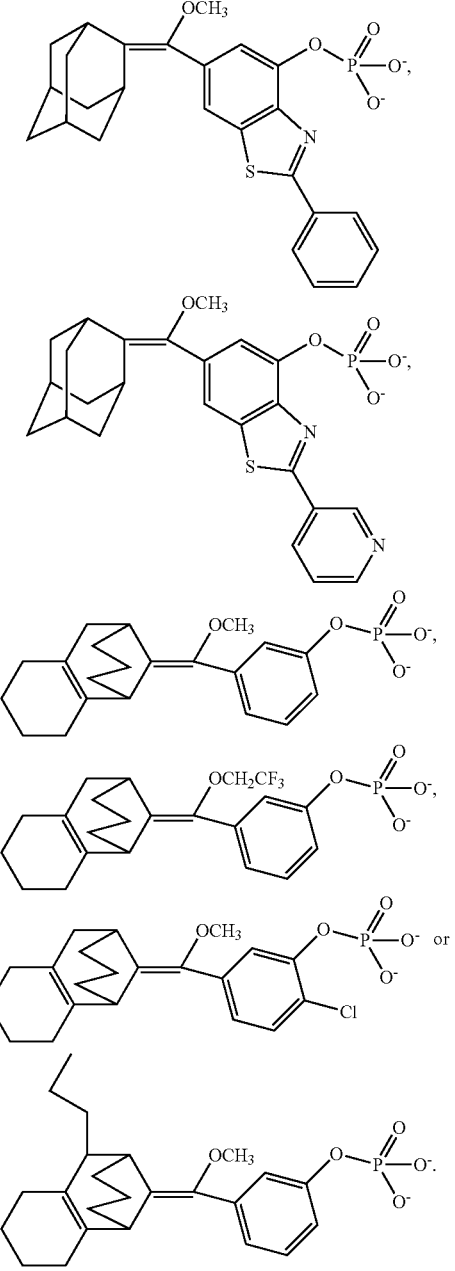

In another step of these methods, an aqueous solution, the oxidant, and the enol ether are combined to form an aqueous solution comprising a 1,2-dioxetane enzyme substrate. The aqueous solution may comprise water, one or more buffer components, one or more organic solvents, one or more coloring agents, one or more preservatives, or combinations thereof. The determination of the concentrations of the oxidant and enol ether in the aqueous solution needed to provide a 1,2-dioxetane enzyme substrate is within the skill of one with ordinary skill in the diagnostic arts.

In another step of these methods, an enzyme complex is provided which is comprised of an enzyme moiety which is capable of cleaving the 1,2-dioxetane enzyme substrate. The enzyme moiety may be an enzyme, enzyme-linked antibody, enzyme-linked antigen or enzyme-linked oligonucleotide.

The enzyme moiety comprises an enzyme which is capable of cleaving the 1,2-dioxetane enzyme substrate. In some embodiments, the enzyme may be a hydrolytic enzyme. A hydrolytic enzyme includes enzymes which cleave ester bonds and is classified as EC 3.1 or cleave sugar bonds and is classified as EC 3.2, and includes, but is not limited to, alkaline phosphatase, β-galactosidase, β-glucosidase, β-glucuronidase or neuraminidase.

Samples will be assayed which are suspected of comprising an enzyme, antigen or a nucleic acid. The sample may be of a biological or non-biological origin. Where the sample is of a biological origin, it may be blood, serum, plasma, urine, feces, saliva, mucus, seminal fluid, tissue, a tissue extract, cell culture media, cells, cell extracts, and the like.

In some embodiments, the enzyme moiety may be an enzyme. In these embodiments, the enzyme in a sample will comprise the enzyme complex. The enzyme complex is contacted with the 1,2-dioxetane enzyme substrate to form a reaction mixture and the reaction mixture is allowed to generate light.

In some embodiments, the emission of light may be detected and such emission will be indicative of the presence of the enzyme, and the amount of light emitted can be correlated to the amount of the enzyme present in the sample.

In some embodiments, the enzyme moiety may be an enzyme-linked antibody. The enzyme-linked antibody comprises a first antibody capable of binding to an antigen and an enzyme capable of cleaving the 1,2-dioxetane enzyme substrate so that the substrate decomposes and generates light. In these embodiments, the enzyme-linked antibody, antigen, and a second antibody which is capable of binding the antigen and immobilized on a solid phase comprises the enzyme complex. The enzyme complex is contacted with the 1,2-dioxetane enzyme substrate to form a reaction mixture and the reaction mixture is allowed to generate light.

In some embodiments, a sample suspected of comprising an antigen may be contacted with an enzyme-linked antibody comprising a first antibody and an enzyme and a solid phase comprising a second antibody, where both antibodies are capable of binding the antigen to provide an enzyme complex which is capable of cleaving the 1,2-dioxetane enzyme substrate so that the substrate decomposes and generates light. The sample, enzyme-linked antibody and solid phase may be combined in any order.

In some embodiments, the method may further comprise the step of removing any unbound enzyme-linked antibody from the enzyme complex by washing the enzyme complex. This may be performed by addition and removal of a buffer compatible with the components of the enzyme complex. Such buffers are well known in the diagnostic arts. Additional wash steps of the solid phase may be performed.

The first antibody, second antibody, or both may be a polyclonal, monoclonal or recombinant antibody.

The solid phase may be a bead, test tube, multi-well plate, microarray, gel, membrane, microparticles, nanocrystals, quantum dots and the like. The materials from which these solid phases are made are known in the diagnostic arts.

The second antibody may be immobilized on the solid phase by non-covalent or covalent attachment of the antibody to the solid phase, by techniques known in the diagnostic arts.

The first antibody may be linked to the enzyme covalently or non-covalently. When linked non-covalently, first antibody is covalently linked to a label and the enzyme is covalently linked to a molecule capable of non-covalent binding to the label.

In some embodiments, the label may be biotin, or biotin derivative, and the molecule may be avidin or strepavidin. A biotin derivative is a biotin molecule which has substitutions. A biotin molecule wherein a portion of biotin structure is missing is also considered a biotin derivative. Biotin derivatives include naturally-occurring biotin as well as synthetic biotin which are substituted.

In some embodiments, the label may be a hapten and the molecule may be an antibody capable of binding to the hapten. The use of digoxigenin as a hapten, and anti-digoxigenin as the molecule is known in the diagnostic arts.

In some embodiments, the enzyme moiety may be an enzyme-linked antigen. The enzyme-linked antigen comprises the antigen and an enzyme capable of cleaving the 1,2-dioxetane enzyme substrate. In these embodiments, the enzyme complex comprises the enzyme-linked antigen bound to solid phase comprising an antibody which is capable of binding the antigen. The enzyme complex is contacted with the 1,2-dioxetane enzyme substrate to form a reaction mixture and the reaction mixture is allowed to generate light.

In some embodiments, a sample suspected of comprising an antigen may contacted with the enzyme-linked antigen, and the solid phase comprising an antibody capable of binding to the antigen. The sample, enzyme-linked antigen and solid phase may be combined in any order.

In some embodiments, the methods may further comprise the step of removing any unbound enzyme-linked antigen from the enzyme complex by washing the enzyme complex. This may be performed by addition and removal of a buffer compatible with the components of the enzyme complex. Such buffers are well known in the diagnostic arts. Additional wash steps of the solid phase may be performed.

The antibody may be a polyclonal, monoclonal or recombinant antibody.

The solid phase may be a bead, test tube, multi-well plate, microarray, gel, membrane, microparticles, nanocrystals, quantum dots and the like. The materials from which these solid phases are made are known in the diagnostic arts.

The antibody may be immobilized to the solid phase by non-covalent or covalent attachment of the antibody to the solid phase.

The antigen may be linked to the enzyme covalently or non-covalently. When linked non-covalently, the antigen may covalently linked to a label and the enzyme may be covalently linked to a molecule capable of non-covalent binding to the label.

In some embodiments, the label may be biotin, or biotin derivative, as described above, and the molecule may be avidin or strepavidin.

In some embodiments, the label may be a hapten and the molecule may be an antibody capable of binding to the hapten. The use the digoxigenin as a hapten, and anti-digoxigenin as the molecule is known in the diagnostic arts.

In some embodiments, the enzyme moiety is enzyme-linked oligonucleotide. The enzyme-linked oligonucleotide comprises an oligonucleotide capable of hydridizing to certain nucleic acid and an enzyme capable of cleaving the 1,2-dioxetane enzyme substrate. In these embodiments, the enzyme complex comprises the enzyme-linked oligonucleotide hybridized to a solid phase comprising the nucleic acid. The enzyme complex is contacted with the 1,2-dioxetane enzyme substrate to form a reaction mixture and the reaction mixture is allowed to generate light.

In some embodiments, the methods may further comprise the steps of providing a sample suspected of comprising a nucleic acid; immobilizing the nucleic acid onto a solid phase; contacting the immobilized nucleic acid and the enzyme-linked oligonucleotide to form an enzyme complex; and, detecting the light emitted from the reaction mixture after addition of the aqueous solution of the 1,2-dioxetane enzyme substrate, wherein the emission of light is indicative of the presence of the nucleic acid, and the amount of light emitted can be correlated to the amount of the nucleic acid present in the sample.

In some embodiments, the method may further comprise the step of removing any unbound enzyme-linked oligonucleotide from the enzyme complex by washing the enzyme complex. This may be performed by addition and removal of a buffer compatible with the components of the enzyme complex. Such buffers are well known in the diagnostic arts. Additional washes of the solid phase may be performed.

The solid phase may be a bead, test tube, multi-well plate, microarray, gel, membrane, microparticles, nanocrystals, quantum dots and the like. The materials from which these are made are known in the diagnostic arts.

The oligonucleotide may be linked to the enzyme covalently or non-covalently. When linked non-covalently, the oligonucleotide may be covalently linked to a label and the enzyme may be covalently linked to a molecule capable of non-covalent binding to the label.

In some embodiments, the label may be biotin, or biotin derivative, as described above, and the molecule may be avidin or strepavidin.

In some embodiments, the label may be a hapten and the molecule may be an antibody capable of binding to the hapten. The use the digoxigenin as a hapten, and anti-digoxigenin as the molecule is known in the diagnostic arts.

In another step of this method, the sample is contacted with the aqueous solution comprising the 1,2-dioxetane enzyme substrate to form a reaction mixture.

In some embodiments, the sample may be added to the aqueous solution comprising the 1,2-dioxetane enzyme substrate, while in other embodiments the aqueous solution comprising the 1,2-dioxetane enzyme substrate may be added to the sample.

In some embodiments, the reaction mixture may further comprise an enhancer. The enhancer may comprise CTAB (cetyltrimethylammonium bromide) and other micelle-forming substances. The enhancer may comprise a polymeric quaternary ammonium salt, polymeric quaternary phosphonium salt or a combination thereof. The polymeric quaternary ammonium salt may be poly(vinylbenzyltrimethylammonium chloride), poly[vinylbenzyl(benzyldimethylammonium chloride)], poly[vinyl(benzyltributylammonium chloride)], poly[vinyl(benzyltripentylammonium chloride)] or a combination thereof. The polymeric quaternary phosphonium salt may be poly(vinylbenzyltrimethylphosphonium chloride), poly(vinylbenzyltributylphosphonium chloride), poly(vinylbenzyltrioctylphosphonium chloride), copolymer comprising poly(vinylbenzyltributylphosphonium chloride) and poly(vinylbenzyltrioctylphosphonium chloride), or a combination thereof.

In some embodiments, the enhancer may further comprise an acceptor dye. Amongst these embodiments, the acceptor dye may be a fluorescent dye. In some of these embodiments, the fluorescent dye may be fluorescein.

In another step of these methods, the reaction mixture is allowed to generate light.

In some embodiments, the light may be observed with the eye or measured using X-ray film or instruments capable of detecting and measuring the light generated. Instruments capable of detecting and measuring the light generated will include, but is not limited to, a luminometer, camera with film or a charge-coupled camera.

Viewed from another aspect, the present invention provides kits for detecting the presence or amount of an analyte in a sample comprising an oxidant and an enol ether having the structure [1], both defined as above.

In some embodiments, the oxidant may be selected from hydrogen peroxide, sodium molybdate, hydrogen peroxide and sodium molybdate, hypochlorite, hypochlorite and hydrogen peroxide, aryl endoperoxide, calcium peroxide peroxyhydrate, and combinations thereof. In some of these embodiments, the oxidant may be hydrogen peroxide, or hydrogen peroxide and sodium molybdate.

In some embodiments, the kits may further comprise an enhancer as described above. In some embodiments, the kits may further comprise an acceptor dye as described above.

In some embodiments, the kit may further comprise instructions for using its components.

The following examples are intended to illustrate but not limit the invention.

Example 1

General Synthesis of Enol Ether Phosphates a. Synthesis of Enol Ether Triester Phosphate.

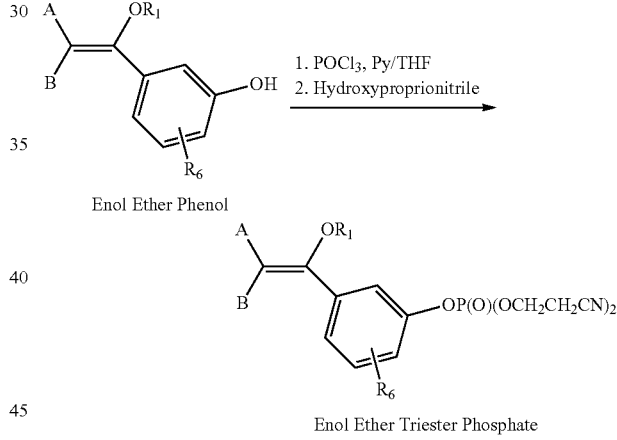

A, B, $R_1$ and $R_6$ are as defined in the Detailed Description of the Invention.

Phosphorus oxychloride (1.5 equiv) is added slowly to pyridine (0.7 ml/mmole phenol enol ether, dried over basic aluminum oxide overnight) at 0° C. under an argon atmosphere. A little bit of white smoke is noticed, but no precipitate forms. To this POCl$_3$ solution is added a solution of the phenol enol ether (30 mmole, 1 equiv) in anhydrous THF (3 ml/mmole phenol enol ether) via dropping funnel over 90 minutes. White pyridine hydrochloride precipitate forms during the addition. An extra volume of THF is used to rinse the storage bottle and dropping funnel, and added to the reaction mixture. The suspension is stirred at 0° C. for 15 minutes and room temperature for 3 hrs. The reaction mixture is then cooled back to 0° C. and 3-hydroxypropionitrile (3.95 equiv) is added slowly in a thin stream via syringe. After stirring at 0° C. for 5 minutes, the mixture is stirred at room temperature overnight, while more white precipitate drops out. The precipitate is removed by filtration and rinsed with EtOAc in hexanes. The combined filtrates are concentrated under reduced pressure to yield a light yellow oil.

To the crude product is added saturated NaHCO$_3$ solution (13 ml/mmole phenol enol ether), and then adequate water is added to dissolve any salt present. The aqueous solution is extracted 3 times with 60% EtOAc in hexanes. The combined organic solutions are washed sequentially with water and brine, dried over anhydrous Na$_2$SO$_4$, and concentrated by rotary evaporator. The gummy crude product is triturated three times with 5% EtOAc in hexanes (heated, cooled to room temperature, then 0° C.). TLC shows that most of the residual pyridine, and traces of the unreacted starting phenol enol ether and the minor bis-aryl monocyanoethyl phosphate triester byproducts, are removed by trituration. The product is then pumped under vacuum to a gum of constant weight.

b. Synthesis of Enol Ether Phosphates.

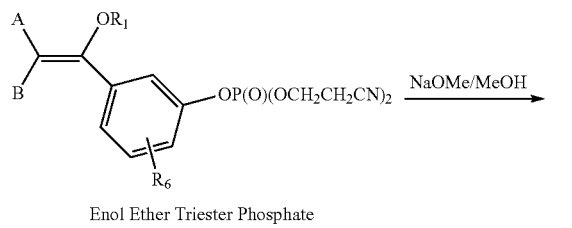

Enol Ether Triester Phosphate

Enol Ether Phosphate

A, B, R$_1$ and R$_6$ are as defined in the Detailed Description of the Invention.

To a solution of the phosphate triester enol ether (28 mmole, 1 equiv) in anhydrous MeOH (3 ml/mmole triester phosphate), is added 4.37 M NaOMe in MeOH solution (2 equiv) in a thin stream via syringe at 0° C. under an argon atmosphere. The mixture is stirred at 0° C. for several minutes and then warmed to room temperature. Heavy precipitation forms while stirring at room temperature. The flask is tapped occasionally to knock the depositing solid back into the stirring solution. The thick suspension is stirred overnight. The reaction mixture is placed on a rotary evaporator to remove approximately half of the MeOH volume, and to the remaining suspension is added 1.5% water/acetone (7 ml/mmole triester phosphate). An additional volume of acetone (7 ml/mmol triester phosphate) is added to transfer most of the powder to a filter. The filter cake is rinsed with cold acetone (2 ml/mmole triester phosphate), and pumped to dryness in a vacuum desiccator to yield white powder.

The crude powder is further purified by dissolving it in water (0.35 ml/mmole triester phosphate), and filtering the solution on a Buchner funnel. An additional volume of water (0.35 ml/mmole triester phosphate) is used to rinse the storage container and filtration funnel, and is filtered. The combined filtrates are then transferred to a freezer bottle, and an additional volume of water (0.35 ml/mmole triester phosphate) is used to rinse the filter flask and added to the solution. When the combined aqueous solutions are added to acetone (13 ml/mmole triester phosphate), a heavy precipitate drops out of the solution. An additional volume of acetone (1.4 ml/mmole trieser phosphate) is added to dilute the suspension for easier filtration. The suspension is allowed to stand on the bench for 30 minutes, and the white precipitate is then collected by filtration. The filter cake is washed with acetone multiple times and dried in a vacuum desiccator to a white powder of constant weight.

Example 2

Synthesis of AMPPD Enol Ether Phosphate

Synthesis AMPPD Enol Ether Phenol is reported in U.S. Pat. No. 5,177,241.

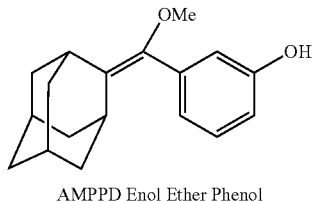 [SMILES: COC(=C1C2CC3CC(C2)CC1C3)c1cccc(O)c1]

AMPPD Enol Ether Phenol b. Synthesis of AMPPD Enol Ether Triester Phosphate.

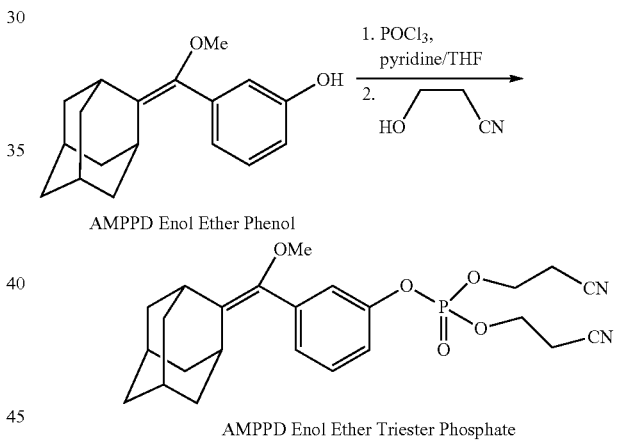

AMPPD Enol Ether Triester Phosphate

Phosphorus oxychloride (1.5 equiv) is added slowly to pyridine (0.7 ml/mmole phenol enol ether, dried over basic aluminum oxide overnight) at 0° C. under an argon atmosphere. No precipitate forms. To this POCl$_3$ solution is added a solution of the AMPDD Enol Ether Phenol (30 mmole, 1 equiv) in anhydrous THF (3 ml/mmole phenol enol ether) via dropping funnel over 90 minutes. White pyridine hydrochloride precipitate forms during the addition. An extra volume of THF is used to rinse the storage bottle and dropping funnel, and added to the reaction mixture. The suspension is stirred at 0° C. for 15 minutes and room temperature for 3 hrs. The reaction mixture is then cooled back to 0° C. and 3-hydroxypropionitrile (3.95 equiv) is added slowly in a thin stream via syringe. After stirring at 0° C. for 5 minutes, the mixture is stirred at room temperature overnight, while more white precipitate drops out. The precipitate is removed by filtration and rinsed with EtOAc in hexanes. The combined filtrates are concentrated under the reduced pressure to yield a light yellow oil. To the crude product is added saturated NaHCO$_3$ solution (13 ml/mmole phenol enol ether), and then adequate water is added to dissolve any salt present. The aqueous solution is extracted 3 times with 60% EtOAc in hexanes. The combined organic solutions are washed sequentially with water and brine, dried over anhydrous Na$_2$SO$_4$, and concentrated by rotary evaporator. The gummy crude product is triturated three times with 5% EtOAc in hexanes (heated, cooled to room temperature, then 0° C.). TLC shows that most of the residual pyridine, and traces of the unreacted starting enol ether phenol and the minor bis-aryl mono-cyanoethyl phosphate triester byproducts, are removed by trituration. The product is then pumped under vacuum to a gum of constant weight.

c. Synthesis of AMPPD Enol Ether Phosphate.

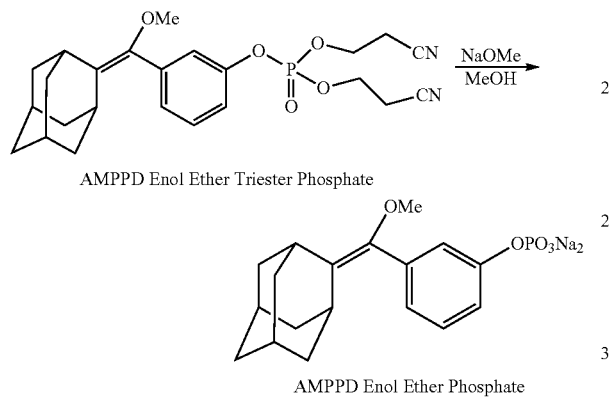

AMPPD Enol Ether Triester Phosphate

AMPPD Enol Ether Phosphate

To a solution of the AMPPD Enol Ether Triester Phosphate (28 mmole, 1 equiv) in anhydrous MeOH (3 ml/mmole triester phosphate), is added 4.37 M NaOMe in MeOH solution (2 equiv) in a thin stream via syringe at 0° C. under an argon atmosphere. The mixture is stirred at 0° C. for several minutes and then warmed to room temperature. Heavy precipitation forms while stirring at room temperature. The flask is tapped occasionally to knock the depositing solid back into the stirring solution. The thick suspension is stirred overnight. The reaction mixture is placed on a rotary evaporator to remove approximately half of the MeOH volume, and to the remaining suspension is added 1.5% water/acetone (7 ml/mmole triester phosphate). An additional volume of acetone (7 ml/mmol triester phosphate) is added to transfer most of the powder to a filter. The filter cake is rinsed with cold acetone (2 ml/mmole triester phosphate), and pumped to dryness in a vacuum desiccator to yield white powder.

The crude powder is further purified by dissolving it in water (0.35 ml/mmole triester phosphate), and filtering the solution on a Buchner funnel. An additional volume of water (0.35 ml/mmole triester phosphate) is used to rinse the storage container and filtration funnel, and is filtered. The combined filtrates are then transferred to a freezer bottle, and an additional volume of water (0.35 ml/mmole triester phosphate) is used to rinse the filter flask and added to the solution. When the combined aqueous solutions are added to acetone (13 ml/mmole triester phosphate), a heavy precipitate drops out of the solution. An additional volume of acetone (1.4 ml/mmole trieser phosphate) is added to dilute the suspension for easier filtration. The suspension is allowed to stand on the bench for 30 minutes, and the white precipitate is then collected by filtration. The filter cake is washed with acetone multiple times and dried in a vacuum desiccator to a white powder of constant weight.

Example 3

Synthesis of ADP-Star Enol Ether Phosphate and ADP-Star®

Phosphonate synthesis is reported in U.S. Pat. No. 5,582, 980, col. 5, lines 18-62.

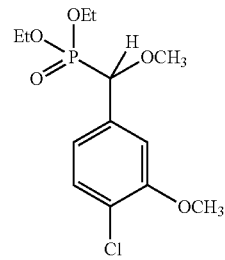 [SMILES: CCOP(=O)(OCC)C(OC)c1ccc(Cl)c(OC)c1]

c. Synthesis of ADP-Star Methoxy Enol Ether.

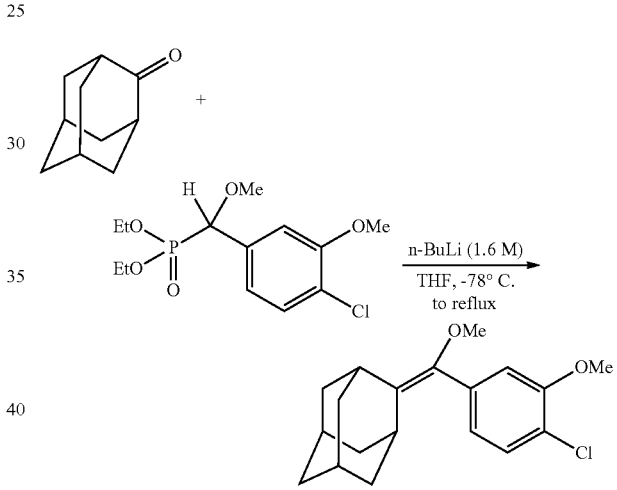

A solution of diethyl 1-methoxy-1-(4-chloro-3-methoxyphenyl)methane phosphonate (21.1 g, 65.4 mmole, 1.1 equiv) in 140 ml of anhydrous THF was cooled to −78° C. under an argon atmosphere and treated with 41 ml (1.6 M, 65.4 mmole, 1.1 equiv) of n-butyllithium in hexanes via dropping funnel for over 20 minutes. The resulting orange reaction mixture was stirred at −78° C. for 15 minutes and then powdered 2-adamantanone (8.93 g, 59.5 mmole) was added in one portion. The reaction mixture was stirred at −78° C. for 40 minutes, then warmed to room temperature and finally heated to reflux for 1.5 hours taking care for any violent butane evolution. The reaction mixture was cooled back to room temperature and kept at this temperature overnight. Next morning, the volatiles in the reaction mixture were removed by rotary evaporation. The residue was then partitioned between saturated NaHCO$_3$ solution and 5% EtOAc in hexanes. The aqueous solution was extracted three times with 5% EtOAc in hexanes (a total of 300 ml). The combined organic solutions were washed with brine, dried over anhydrous Na$_2$SO$_4$ and passed through a silica gel plug. After concentration of the filtrate, a yellow oil was obtained. The crude product was crystallized in 30 ml of MeOH. After the second re-crystallization in 20 ml of MeOH, 11.99 g (63.2%) of a slightly yellow solid was obtained. The combined mother liquors were further purified by silica gel chromatography (0-4% EtOAc in hexanes) and crystallization twice in 8 ml of MeOH, to yield the second crop of product, 1.74 g (9.2%) as a slightly yellow solid. IR (CHCl$_3$): 3005, 2910, 2850, 1590, 1573, 1482, 1463, 1448, 1398, 1308, 1280, 1248, 1098, 1090, 1080, 1063, 1028, 865, 824 cm$^{-1}$. $^1$H NMR (400 MHz, CDCl$_3$): δ 7.31 (d, J=8.3 Hz, 1H), 6.92 (d, J=1.8 Hz, 1H), 6.84 (dd, J=8.2, 1.8 Hz, 1H), 3.90 (s, 3H), 3.31 (s, 3H), 3.25 (br. s, 1H), 2.64 (br. s, 1H), 1.72-2.03 (m, 12H).

d. Synthesis of ADP-Star Enol Ether Phenol.

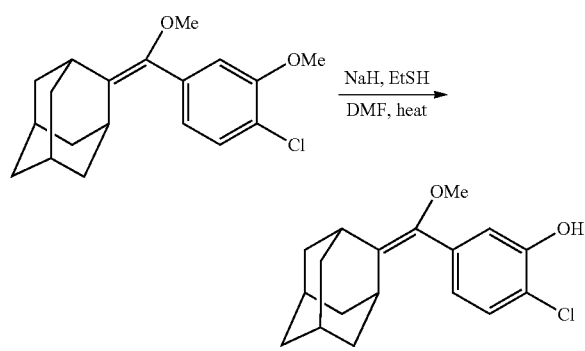

NaH (60% in mineral oil, 1.63 g, 40.8 mmole, 1.3 equiv) was rinsed with hexanes 3 times (3×15 ml), the resulting wet NaH powder was blown to dryness by a stream of argon air and pumped under vacuum briefly for 5 minutes. To a suspension of powdered NaH in anhydrous DMF (35 ml), was added EtSH (3.1 ml, 42.3 mmole, 1.35 equiv) dropwise via syringe over 10 minutes at 0° C. under an argon atmosphere. Violent gaseous evolution occurred immediately during the addition; the resulting clear sodium ethylthiolate solution was stirred at 0° C. for 5 minutes and room temperature for 25 minutes. The solution was cooled back to 0° C., and the sodium ethylthiolate solution was treated with solid ADP-Star methoxy enol ether (10 g, 31.4 mmole) in one portion. The suspension was heated to reflux at 120~125° C.; a homogeneous mixture resulted during the heating and became cloudy later during the refluxing. After 2 hours of refluxing, TLC showed the reaction was complete. The reaction mixture was cooled back to room temperature and quenched with saturated NaHCO$_3$ solution. The aqueous solution was extracted 3 times with 20% EtOAc in hexanes (a total of 150 ml). The combined organic solutions were washed with brine, dried over anhydrous Na$_2$SO$_4$ and passed through a coarse silica gel (40-140 mesh) plug. The filtrate was concentrated by rotary evaporation to yield a white powder with a mild stench. The crude product was purified by trituration. Upon heating with 30 ml of hexanes, followed by cooling and storing in refrigerator overnight, 8.78 g (91.8%) of the product was obtained as a white solid after filtration.

IR (CHCl$_3$): 3540, 3280, 2998, 2910, 2850, 1573, 1482, 1445, 1342, 1309, 1192, 1170, 1090, 1046, 1007, 876, 821 cm$^{-1}$. $^1$H NMR (400 MHz, CDCl$_3$): δ 7.28 (d, J=8.1 Hz, 1H), 6.98 (d, J=2.2 Hz, 1H), 6.84 (dd, J=8.1, 2.2 Hz, 1H), 5.58 (s, 1H, OH), 3.30 (s, 3H), 3.23 (br. s, 1H), 2.65 (br. s, 1H), 1.71-2.00 (m, 12H).

e. Synthesis of ADP-Star Enol Ether Triester Phosphate.

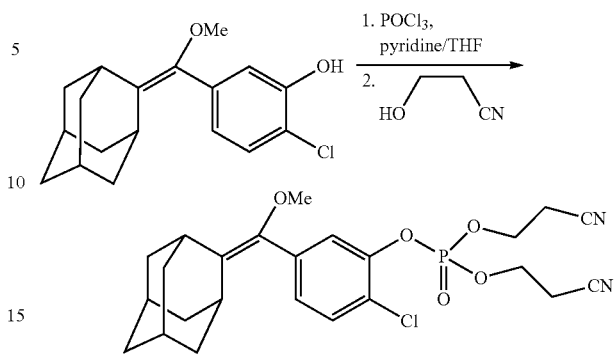

Phosphorus oxychloride (4.2 ml, 46.3 mmole, 1.5 equiv) was added slowly to pyridine (22 ml, dried over basic aluminum oxide overnight) at 0° C. under an argon atmosphere. A little bit of white smoke was noticed, but no precipitate formed. To this POCl$_3$ solution was added a solution of the ADP-Star Enol Ester Phenol (9.41 g, 30.87 mmole) in 94 ml of anhydrous THF via dropping funnel over 90 minutes. White pyridine hydrochloride precipitate formed during the addition. An extra 10 ml of THF was used to rinse the storage bottle and dropping funnel, and added to the reaction mixture. The suspension was stirred at 0° C. for 15 minutes and room temperature for 2 hours and 40 minutes. The reaction mixture was then cooled back to 0° C. and 3-hydroxypropionitrile (8.3 ml, 122 mmole, 3.95 equiv based on the phenol) was added slowly in a thin stream via syringe. After stirring at 0° C. for 5 minutes, the mixture was stirred at room temperature overnight (~15.5 hours), while more of white precipitate dropped out. The precipitate was removed by filtration and rinsed with 60 ml of EtOAc in hexanes. The combined filtrates were concentrated under the reduced pressure to yield a light yellow oil.

The crude product was added to 400 ml of saturated NaHCO$_3$ solution and then adequate water was added to dissolve any salt present. The aqueous solution was extracted 3 times with 60% EtOAc in hexanes (a total of 400 ml). The combined organic solutions were washed with water and brine (150 ml each), dried over anhydrous Na$_2$SO$_4$ and concentrated by rotary evaporation. The gummy crude product was triturated three times with 40 ml each of 5% EtOAc in hexanes (heated, cooled to room temperature, then to 0° C.). TLC showed most of the residual solvent pyridine, trace of the unreacted starting material ADP-Star enol ether phenol and the minor bis-aryl mono-cyanoethyl phosphate triester byproduct were removed by these triturations. The product was then pumped under vacuum to a constant weight; 13.4 g (92%) was obtained as a light yellow gum.

IR (CHCl$_3$): 3005, 2913, 2850, 2258, 1566, 1481, 1398, 1288, 1177, 1092, 1079, 1045, 1008, 993, 965, 953, 910, 830 cm$^{-1}$. $^1$H NMR (400 MHz, CDCl$_3$): δ 7.40-7.45 (m, 1H), 7.35-7.39 (m, 1H), 7.12-7.18 (m, 1H), 4.38-4.55 (m, 4H), 3.32 (s, 3H), 3.24 (br. s, 1H), 2.79-2.91 (m, 4H), 2.63 (br. s, 1H), 1.73-2.04 (m, 12H).

f. Synthesis of ADP-Star Enol Ether Phosphate.

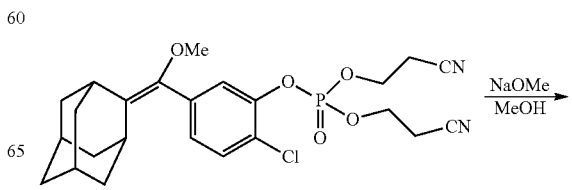

-continued

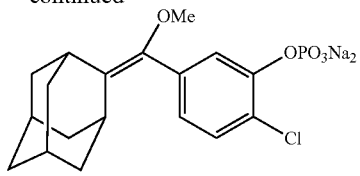

To solution of the ADP-Star Enol Ether Triester Phosphate (13.83 g, 28.2 mmole) in 85 ml of the anhydrous MeOH, was added 4.37 M of NaOMe in MeOH solution (12.9 ml, 56.3 mmole, 2 equiv) in a thin stream via syringe at 0° C. under an argon atmosphere. The mixture was stirred at 0° C. for 2 minutes and then warmed up to room temperature. Heavy precipitation formed while stirring at room temperature. The flask was tapped occasionally to knock the depositing solid back into the stirring solution. The thick suspension was stirred overnight for 17.5 hours. Analytic HPLC monitoring, using the using an acetonitrile/NaHCO$_3$ gradient, showed the desired product at 8.3 minutes; incomplete reaction intermediate mono-cyanoethyl mono-aryl phosphate diester at 13.6 min; byproduct bis-aryl phosphate diester at 16.9 min, and ADP-Star phenol enol ether at 19.6 min. The reaction mixture was placed on a rotary evaporator to remove approximately 45 ml of MeOH, and to the remaining suspension was added 3 ml of water and then 200 ml of acetone. The solution was filtered on a Buchner funnel. An additional 10 ml of water was used to rinse the storage container and filtration funnel, and added to the filtrate. The combined filtrates were then transferred to a one-liter freeze dryer bottle, an additional 10 ml of water was used to rinse the filter flask and added to the solution. When the combined aqueous solution was added 360 ml of acetone, heavy precipitate dropped out of the solution. An additional 40 ml of acetone was added to dilute the suspension for easier filtration later. The suspension was allowed to stand on the bench for 30 minutes, then the white precipitate was collected by filtration. The filter cake was washed with acetone multiple times (a total of 200 ml) and dried in a vacuum desiccator until a constant weight of 10.07 g (83.9%) of a white powder was obtained as the 1$^{st}$ crop of product.

$^1$H NMR (400 MHz, D$_2$O): δ 7.42 (br. s, 1H), 7.38 (d, J=8.2 Hz, 1H), 6.96 (d, J=8.2 Hz, 1H), 3.35 (s, 3H), 3.08 (br. s, 1H), 2.57 (br. s, 1H), 1.68-1.98 (m, 12H).

While the filtrate cooled in the refrigerator, more of precipitate dropped out in the solution. An additional second crop of product, 1.388 g (11.6%) was obtained by filtration. Its proton NMR spectrum was identical to that of the first crop product. The analytic HPLC peak integrals of product from both crops were greater than 99.4%.

g. Synthesis of ADP-Star®.

ADP-Star® is synthesized, following the synthesis for CDP-Star®, reported in U.S. Pat. No. 5,582,980, by substituting 2-Adamantanone for 5-Chloro-2-Adamantanone in the procedure for compound 5, columns 5-6. All other steps are identical to those reported for CDP-Star®.

Other examples of enol ether phosphates that can be used for substrates include, but are not limited to:

Benzthiazole Enol Ether Phosphate and analogues cited within U.S. Pat. No. 6,355,441.

(3-phosphoryloxyphenyl)methoxymethylene tricyclo[7.3.1.0$^{2,7}$]tridec-2,7-ene, disodium salt. U.S. Pat. No. 6,461,876

[(3-Phosphoryloxyphenyl)(2,2,2-trifluoroethoxy)methylene]tricyclo[7.3.1.0$^{2,7}$]tridec-2,7-ene, disodium salt. U.S. Pat. No. 6,461,876.

(3-phosphoryloxy-4-chlorophenyl)methoxymethylene tricyclo[7.3.1.0.sup.2,7]tridec-2,7-ene, disodium salt U.S. Pat. No. 6,461,876.

[(4-Methoxy)-4-(3-phosphoryloxyphenyl)]spiro[1,2-dioxetane-3,13'-(8-n-prop yl)tricyclo[7.3.1,o.sup.2,7]tridec-2,7-ene], disodium salt. U.S. Pat. No. 6,461,876.

(3-phosphoryloxyphenyl) methoxymethylene adamantan-4,5-ene, disodium salt. U.S. Pat. No. 6,461,876.

Example 4

General Synthesis of Enol Ether Glycosides by Phase Transfer Catalysis

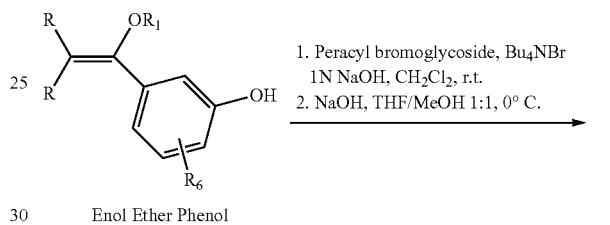

Enol Ether Phenol

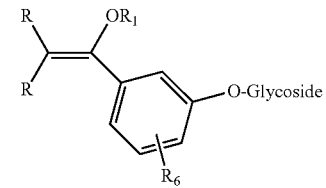

Enol Ether Glycoside

To a vigorously stirred biphasic mixture of the phenol enol ether (1 equiv) and PTC catalyst, Bu$_4$NBr (1.05 equiv), in a mixture of 1N NaOH solution and CH$_2$Cl$_2$, a solution of peracyl glycosyl bromide* (1.5 equiv) in CH$_2$Cl$_2$ was added in a thin stream at room temperature. The mixture was stirred for 60 minutes. Saturated NaHCO$_3$ solution was added to the reaction, and the solution was extracted 3 times with CH$_2$Cl$_2$. The combined CH$_2$Cl$_2$ solution was washed with water, dried over anhydrous Na$_2$SO$_4$, concentrated and purified by silica gel chromatography to give the protected glycosyl enol ether.

The peracyl glycosyl enol ether (1 equiv) is dissolved in 1:1 THF/MeOH, deprotected by adding 1N NaOH at 0° C., and the reaction is then warmed to room temperature. Upon complete deprotection, the reaction is neutralized with solid NaHCO$_3$ stripped of solvents by rotary evaporation, and purified by reverse phase chromatography.

*Examples of peracyl bromoglycosides are: alpha-D-glucopyranosyl bromide, 2,3,4,6-tetraacetate (CAS#572-09-8); alpha-D-galactopyranosyl bromide, 2,3,4,6-tetraacetate (CAS#3068-32-4); alpha-D-glucopyranuronic acid, 1-bromo-1-deoxy-methyl ester, 2,3,4-triacetate (CAS#21085-72-3).

Example 5

Synthesis of Glucon-Star Enol Ether Tetraacetate by Phase Transfer Catalysis a. Synthesis of Glucon-Star Enol Ether Tetraacetate.

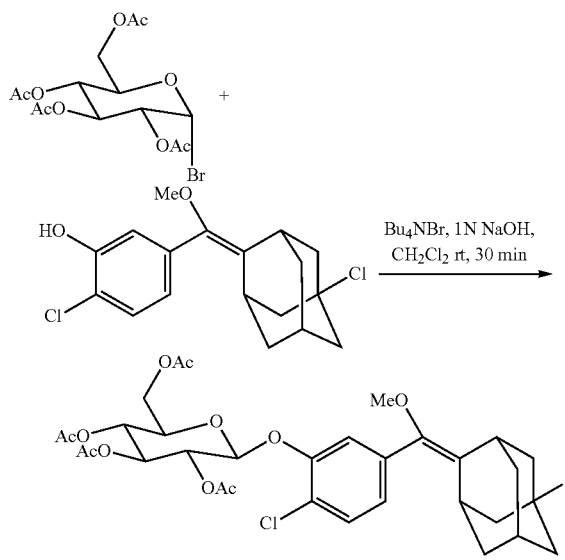

To a vigorously stirred mixture of CDP-Star enol ether phenol (1.02 g, 3 mmole) and PTC catalyst, tetrabutylammonium bromide (1.02 g, 3.15 mmole), in 1N NaOH (20 ml) and 14 ml $CH_2Cl_2$ at room temperature, was added alpha-D-glucopyranosyl bromide, 2,3,4,6-tetraacetate (2.47 g, 6 mmole) in 6 ml $CH_2Cl_2$. The reaction was stirred for 30 minutes until the tlc showed very little starting material left. The reaction was quenched with saturated $NaHCO_3$ solution. The aqueous layer was extracted with $CH_2Cl_2$ three times, and the combined organic layers were washed with brine and dried over anhydrous $Na_2SO_4$. Four drops of triethylamine were added to the solution, and the solution was passed through a short silica gel column, eluting with 100 ml of 40% EtOAc/hexanes, to yield an orange gum.

After overnight storage at 4° C., the crude product was dissolved in a small amount of $CH_2Cl_2$, and chromatographed with silica gel, eluting with 20%-50% EtOAC/hexanes. Fractions with coupled product were collected and concentrated to yield a light yellow gum (2.31 g, >100%).

b. Synthesis of Glucon-Star Enol Ether.

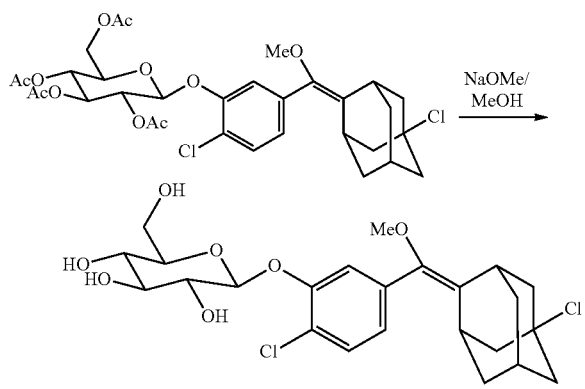

To a solution of the crude Glucon-Star Enol Ether Tetraacetate (1.5 g theoretical yield, 3 mmol), was added 15 drops of 4.37M NaOMe in MeOH by pipette at room temperature. The mixture was stirred overnight, with minimal acetate hydrolysis. An additional 30 drops of 4.37M NaOMe in MeOH was added, the mixture turned from yellow to orange, and the hydrolysis was complete after 4 hrs by TLC. Ammonium chloride (1 g) was added to quench the reaction, and the solution was stirred for 1 hour. Methylene chloride was added to precipitate product, and 5% $MeOH/CH_2Cl_2$ was added until no more precipitate dropped out. The precipitate was collected by filtration and washed with 5% $MeOH/CH_2Cl_2$. The crude gum was purified by silica gel chromatography, eluting first with 30% EtOAc/hexanes to recover CDP-Star Enol Ether Phenol, and then flushing the column with 5-10% $MeOH/CH_2Cl_2$ to yield Glucon-Star Enol Ether as a light yellow foam (1.18 g, 79%).

Example 6

General Synthesis of Enol Ether Glycosides by Schmidt Glycosidation

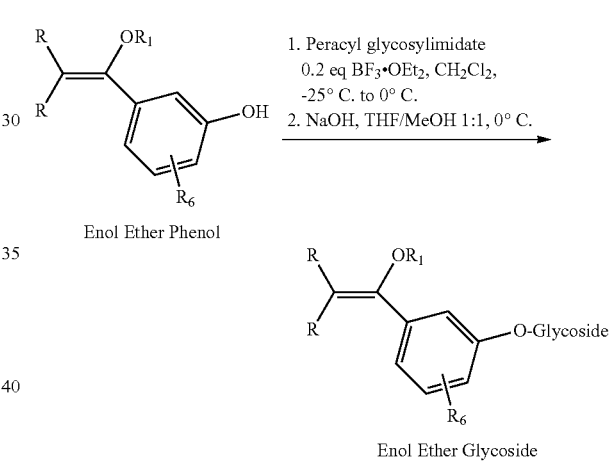

To a stirred solution of the peracyl glycosyl trichloroacetimidate* (1.2-1.5 equiv) in $CH_2Cl_2$ (6 ml/equiv of the phenol) was added solid phenol enol ether (1 equiv) in one portion at room temperature under an argon atmosphere. The mixture was cooled to −23° C. and treated with a solution of $BF_3 \cdot OEt_2$ (0.2 equiv) in $CH_2Cl_2$ (0.6 ml/equiv of the phenol) slowly over 10 minutes. The reaction mixture became cloudy during $BF_3 \cdot OEt_2$ addition, and was slowly warmed to 0° C. over 1.5 hours. The reaction was quenched with $Et_3N$ (5 equiv of $BF_3 \cdot OEt_2$) and stirred at 0° C. for 10 minutes. The reaction mixture was partitioned between saturated $NaHCO_3$ solution and $CH_2Cl_2$, purified by silica gel chromatography, and the peracylated glycosyl enol ether was collected as a foam.

The peracyl glycosyl enol ether (1 equiv) is dissolved in 1:1 THF/MeOH, deprotected by adding 1N NaOH at 0° C., and the reaction is then warmed to room temperature. Upon complete deprotection, the reaction is neutralized with solid $NaHCO_3$ stripped of solvents by rotary evaporation, and purified by reverse phase chromatography.

*Peracyl glycosyl trichloroacetimidate syntheses are reported in a review by R. R. Schmidt, Adv. Carbohydr. Chem. Biochem., 1994, 50:21, and references cited therein.

Example 7

Glucuronosyl Enol Ether Synthesis by Schmidt Glycosidation a. Synthesis of Peracyl Glucuronosyl AMPPD Enol Ether.

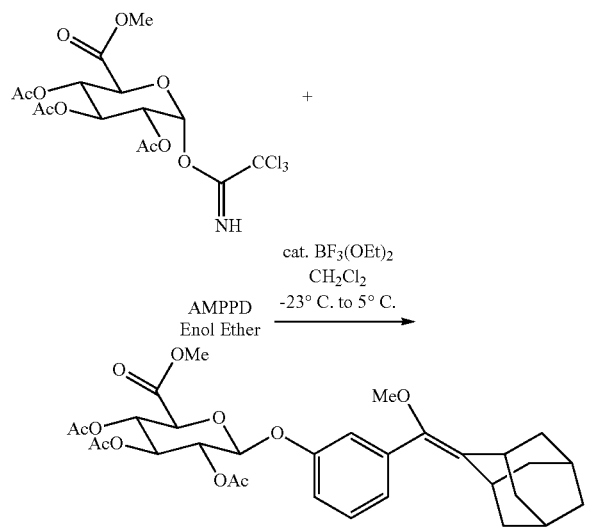

To a solution of the peracyl glucuronosyl trichloroacetimidate (1.2 eq) in $CH_2Cl_2$ (24 ml/equiv), is added solid phenol enol ether (1 equiv) at room temperature under an argon atmosphere. The mixture is cooled to −25° C. and treated with a $CH_2Cl_2$ solution of boron trifluoride etherate (0.2 eq) added slowly over 10 min. The resulting cloudy mixture is stirred at temperature gradients of −23° C. to −20° C. for an hour, −20° C. to −10° C. for 30 minutes and −10° C. to +5° C. for 30 minutes. The reaction is quenched with $Et_3N$ for 15 minutes at +5° C., followed by addition of saturated $NaHCO_3$ solution. The mixture is extracted with $CH_2Cl_2$, washed with water, dried over anhydrous $Na_2SO_4$, and a small amount of $Et_3N$ is added to the organic solution. The crude product is obtained after rotary evaporation and silica gel chromatography.

b. Synthesis of Glucuronosyl AMPPD Enol Ether.

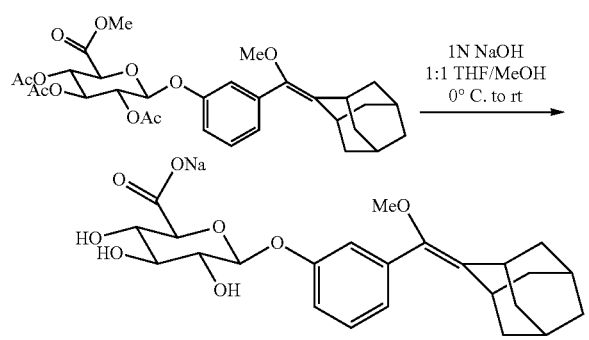

The peracyl glucuronosyl AMPPD enol ether (1 equiv) is dissolved in 1:1 THF/MeOH, deprotected by adding 1N NaOH at 0° C., and then warmed to room temperature. Upon completion of the deprotection, the reaction is neutralized with solid $NaHCO_3$, stripped of solvents by rotary evaporation, and then purified by reverse phase chromatography.

Example 8

Conversion of Enol Ethers to Dioxetanes in Aqueous Solutions

Two enol ether phosphates were successfully converted to their corresponding 1,2-dioxetane alkaline phosphatase substrates by oxidation in aqueous, basic conditions. The 1,2-dioxetanes, AMPPD® and ADP-Star, were generated from enol ether precursors, and subsequently used in alkaline phosphatase detection assays and an IL-6 ELISA (enzyme-linked immunosorbent assay). Model oxidation conditions and demonstration of dioxetane formation are detailed below.

a. Oxidation of AMPPD Enol Ether Phosphate to AMPPD®.

Figure 2:
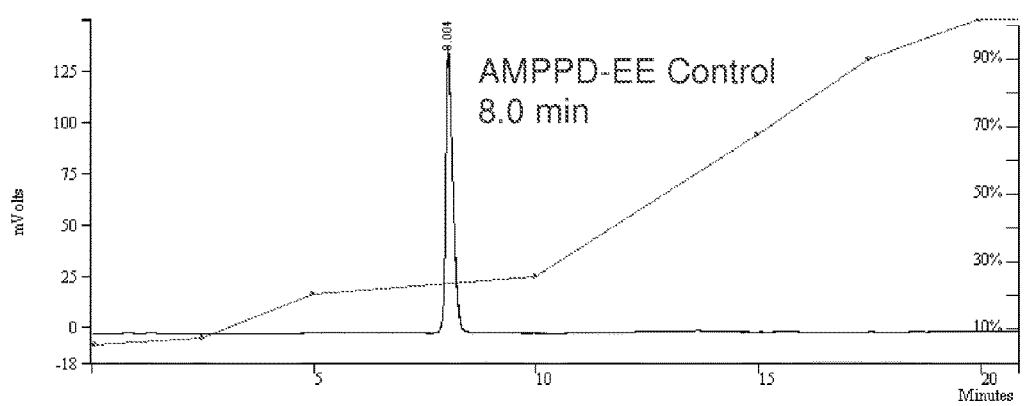
FIG. 2 is an HPLC trace which shows the elution peak of starting material, AMPPD Enol Ether Phosphate (AMPPD-EE) Control.
Figure 3:
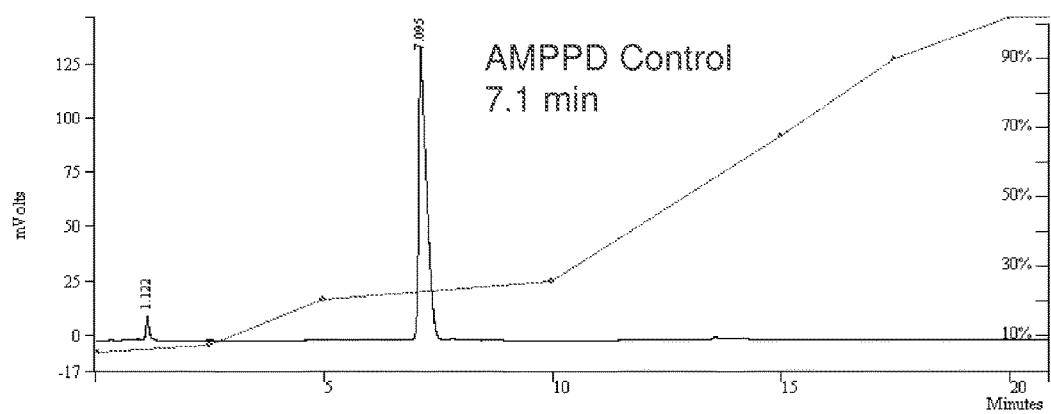
FIG. 3 is an HPLC Trace which shows the elution peak of the desired dioxetane, AMPPD® Control.
Figure 4:
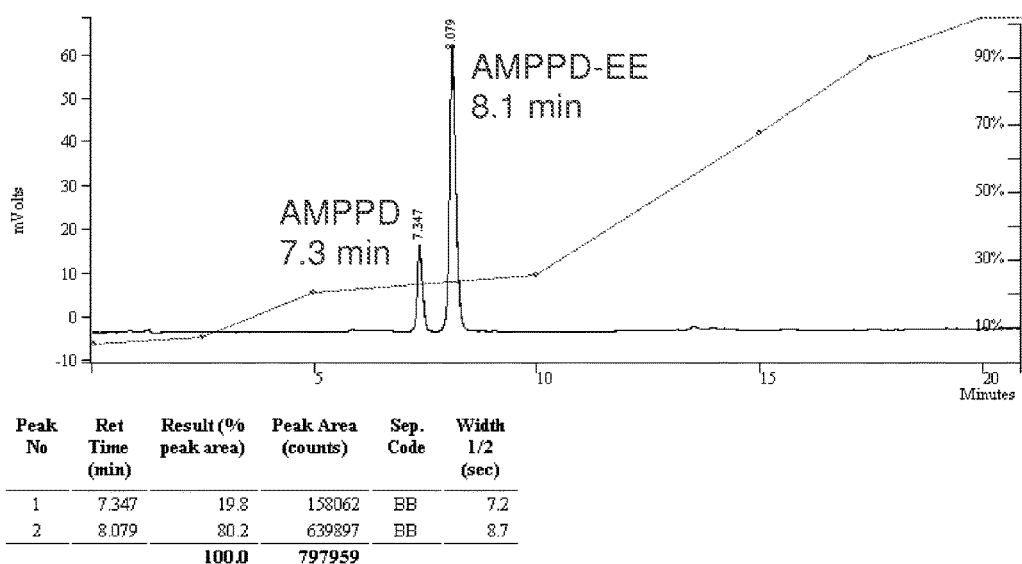
FIG. 4 is an HPLC Trace which shows the elution peaks the Mixed Controls, AMPPD Enol Ether Phosphate (AMPPD-EE) and AMPPD®.
Figure 5:
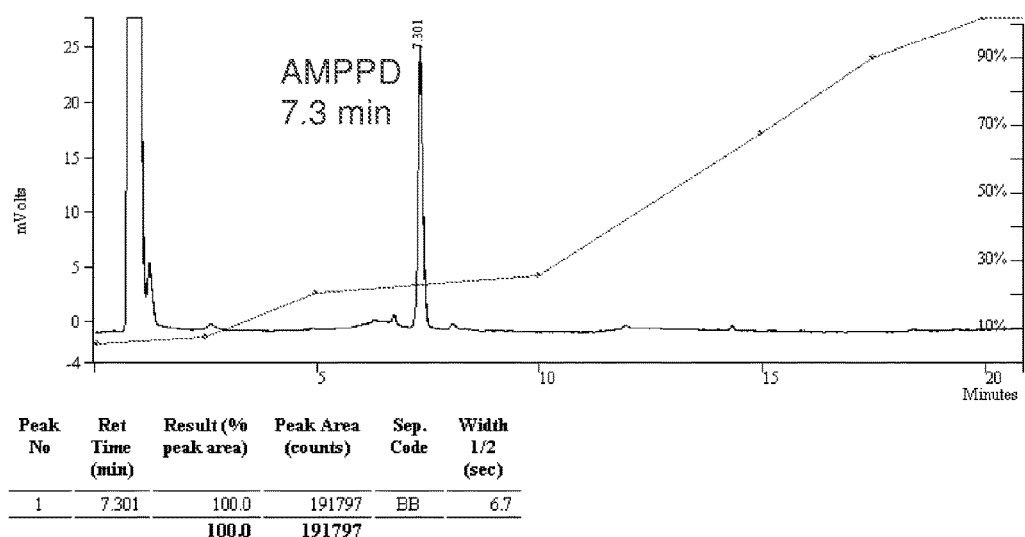
FIG. 5 is an HPLC Trace showing the completed oxidation of AMPPD Enol Ether Phosphate (AMPPD-EE) to AMPPD®.

AMPPD enol ether phosphate (AMPPD-EE) was efficiently oxidized to the 1,2-dioxetane substrate, AMPPD®, in aqueous solution using the oxidation system of $Na_2MoO_4$/$H_2O_2$ at alkaline pH, as shown in the reaction scheme depicted in FIG. 1. The reagents used for this were:
AMP Buffer: 0.1M aminomethylpropanol buffer, pH 9.5.
AMPPD® (Life Technologies), 1 mg/mL in AMP Buffer
AMPPD-EE, 1 mg/mL (2.3 mM) in AMP Buffer (2.5 mM).
$H_2O_2$ stock: 10% (3M) in water (from 50% solution, Aldrich).
$Na_2MoO_4$ stock: 4.8 mg/mL (Aldrich), ~20 mM.
10 µL AMPPD-EE (0.23 mM), 40 µL AMP Buffer, 40 µL, $H_2O_2$ stock (1M) and 20 µL $Na_2MoO_4$ stock (3.6 mM) were combined and allowed to react at 37° C. for one hour, then at 55° C. for ten minutes. The progress of this reaction was followed by HPLC. The HPLC trace of the elution peak of the starting material (AMPPD-EE) is shown in FIG. 2 as the control trace. The HPLC trace of the elution peak of the desired 1,2-dioxetane (AMPPD®) is shown in FIG. 3. HPLC traces of FIG. 4 and FIG. 5 show the progression of oxidation of AMPPD-EE (8.1 min) to the desired dioxetane substrate, AMPPD® (7.3 min). The reaction cleanly gave one product (AMPPD®) in one hour and ten minutes.

b. Oxidation of ADP-Star Enol Ether Phosphate to ADP-Star®.

Figure 6:
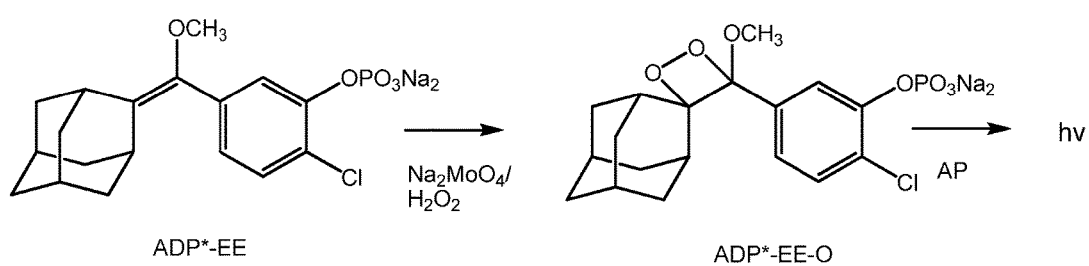
FIG. 6. shows the reaction scheme for conversion of ADP-Star Enol Ether Phosphate (ADP*-EE) to ADP-Star® (ADP*-EE-O), in aqueous solution using the oxidation system of $Na_2MoO_4/H_2O_2$ at alkaline pH, followed by activation of the dioxetane by alkaline phosphatase.

Oxidation of ADP-Star enol ether phosphate (ADP*-EE) to ADP-Star® (ADP*) by $Na_2MoO_4$/$H_2O_2$ at alkaline pH was done according to the reaction scheme shown in FIG. 6. The reagents used were:
AMP Buffer: 0.1M aminomethylpropanol buffer, pH 9.5.
0.1M $Na_2MoO_4$ (Aldrich).
ADP*-EE-O stock: 10 mg ADP*-EE in 2 mL of AMP Buffer combined with 50 µL of 0.1M $Na_2MoO_4$ stock (11.7 mM ADP*-EE with 2.5 mM $Na_2MoO_4$).
$H_2O_2$ stock: 10% (3M) in water (from 50% solution, Aldrich).
100 µL of ADP*-EE-O stock was combined with 40 µL, $H_2O_2$ stock and the mixture allowed to react at 55° C. for one hour. After this time, the reaction mixture was diluted with 0.5 mL AMP Buffer to give a solution containing the 1 mg/mL (2.3 mM) of the resulting 1,2-dioxetane and 0.5 mM $Na_2MoO_4$. This solution is referred to as the ADP*-EE Oxidation mixture. The oxidation of ADP* EE to ADP-Star® was demonstrated by activating the resulting dioxetane with alkaline phosphatase and measuring the light emission on a Turner luminometer. The following reagents were used for this:
0.1M aminomethylpropanol buffer, pH 9.5 (AMP Buffer), CDP-Star® (CDP*, Life Technologies): 6.2 mg/mL (12.5 mM) in AMP Buffer, ADP-Star® (ADP*, Life Technologies): 1 mg/mL (2.2 mM) in 0.1M AMP Buffer,
ADP*-EE Oxidation mixture: 1 mg/mL (2.3 mM) in 0.1M AMP Buffer,
TBQ: 10× Sapphire II™ chemiluminescence enhancer (Life Technologies), and
Alkaline Phosphatase stock (AP): 8 ng/mL (from 17.4 mg/mL concentrate).

10 μL ADP* or ADP*-EE Oxidation mixture (0.22 or 0.23 mM, respectively), 10 μL TBQ, 80 μL AMP Buffer and 10 μL AP were combined and the luminescence from the mixture was measured continuously at 37° C. for 25 minutes. 1.6 μL CDP* (0.2 mM), 10 μL TBQ, 80 μL AMP Buffer and 10 μL AP were combined and the luminescence from the mixture was measured continuously at 37° C. for 25 minutes.

Figure 7:
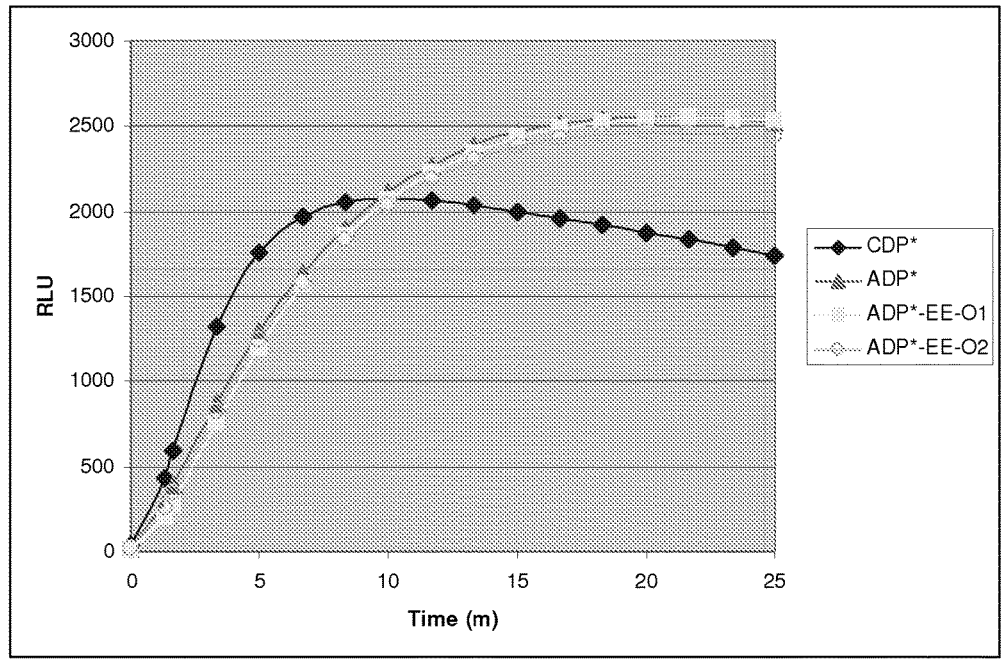
FIG. 7 shows the ADP-Star® emission curves for the activation by alkaline phosphatase of the ADP-Star® (ADP*) dioxetane control, two ADP-Star enol ether (ADP*-EE-O1 and ADP*-EE-O2) oxidations and commercially available CDP-Star® (CDP*) dioxetane control.

FIG. 7 shows the ADP-Star light emission curves (for ADP-Star dioxetane control and two product of the ADP-Star enol ether phosphate oxidations) showed higher light emission than the commercially available CDP-Star® dioxetane control.

Example 9

Thermal Stability of Reagents

Figure 8:
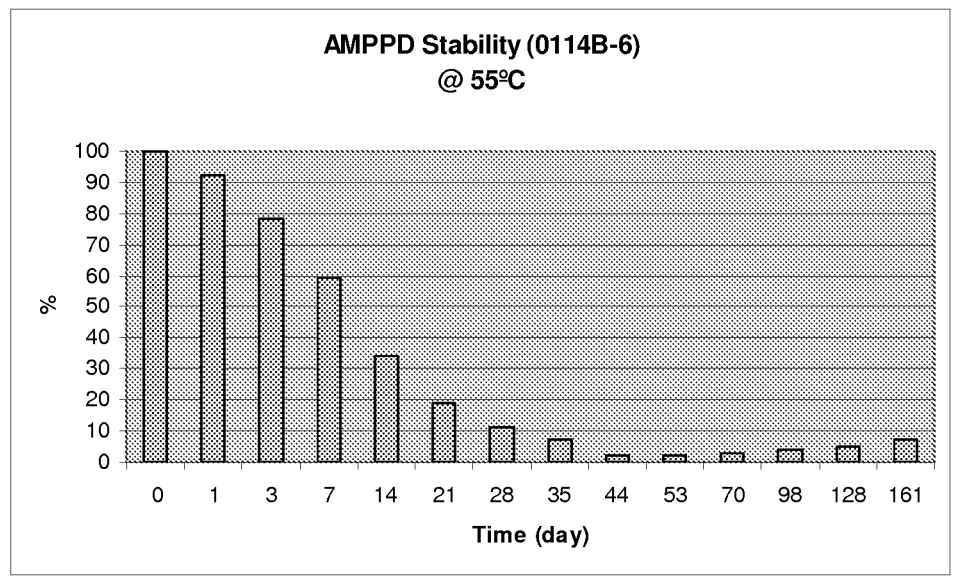
FIG. 8 shows a graph of the thermal stability at 55° C. of AMPPD®.
Figure 9:
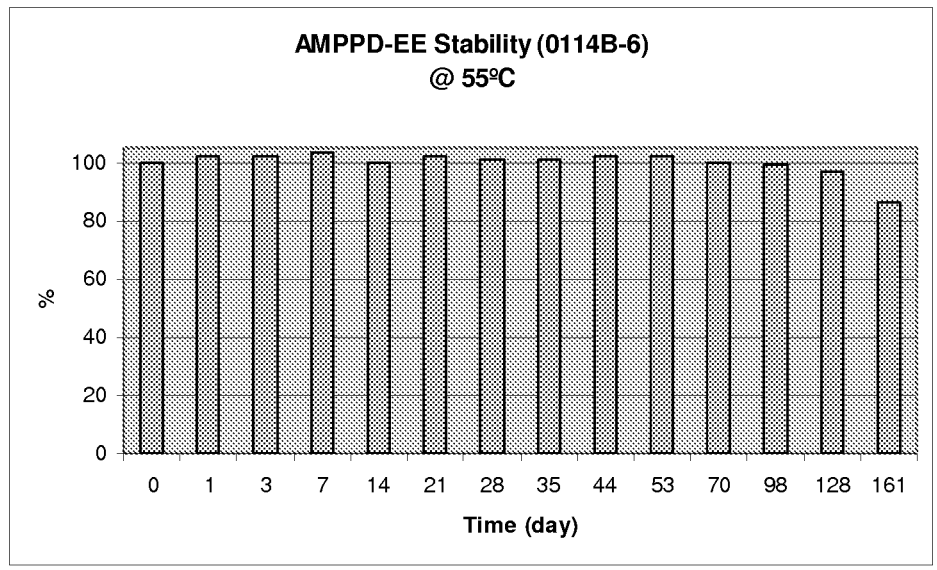
FIG. 9 shows a graph of the thermal stability at 55° C. of AMPPD Enol Ether Phosphate (AMPPD-EE).
Figure 10:
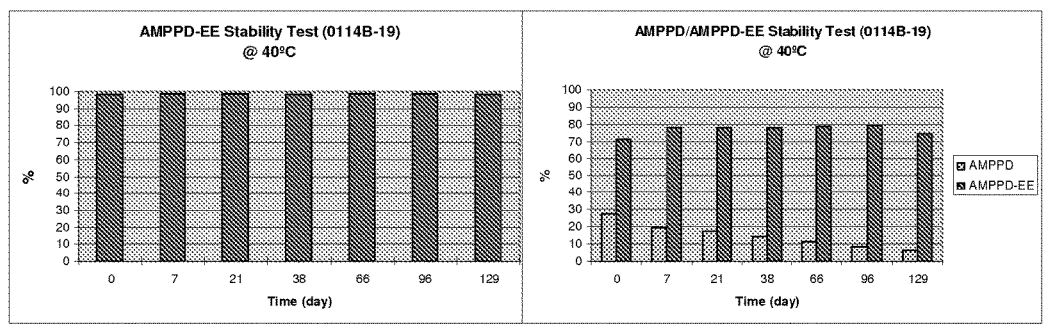
FIG. 10 shows of the thermal stability at 40° C. of AMPPD Enol Ether Phosphate (AMPPD-EE) alone (left graph) and a mixture of AMPPD® and AMPPD Enol Ether Phosphate (AMPPD-EE) (right graph). In the right graph, the bars on the left are data relating to AMPPD®, while the corresponding bar on the right are for data relating to AMPPD-EE.
Figure 11:
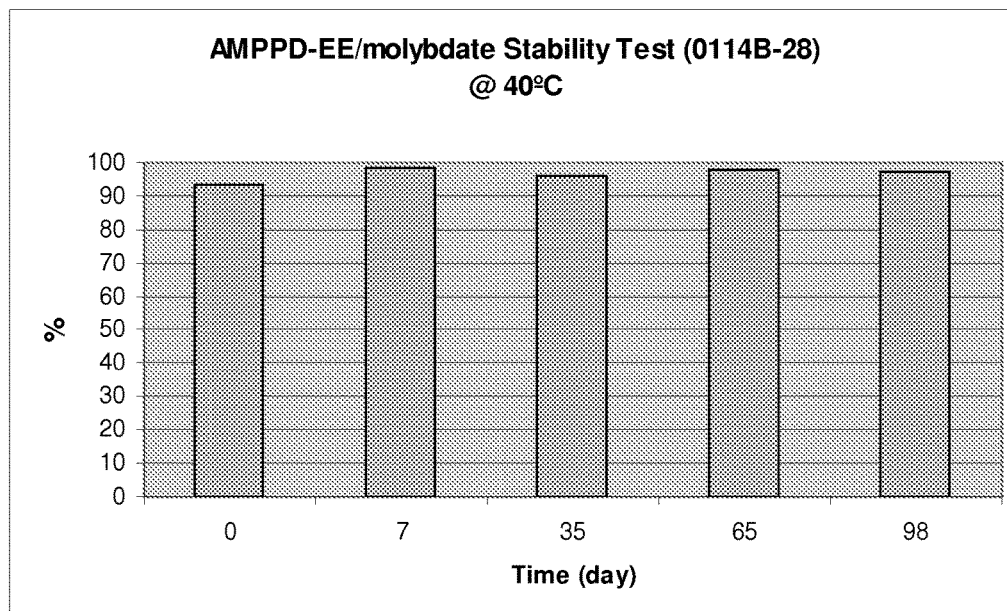
FIG. 11 shows the thermal stability at 40° C. of AMPPD Enol Ether Phosphate (AMPPD-EE) in the Presence of Sodium Molybdate.

The thermal stabilities of aqueous solutions AMPPD®, AMPPD enol ether phosphate (AMPPD-EE) and AMPPD-EE in the presence of $Na_2MoO_4$ were examined. The thermal half-life of AMPPD® at 40° C. is ~40 days, and the half-life drops to ~10 days at 55° C. as is shown in FIG. 8 and FIG. 10. In comparison, the AMPPD enol ether phosphate shows virtually no thermal decomposition at 40° C. over 4+ months, and minimal thermal decomposition at 55° C. over 5+ months as is shown in FIG. 9 and FIG. 10. The thermal stability of AMPPD-EE in the presence of $Na_2MoO_4$ at 40° C. was also examined and no thermal decomposition of AMPPD enol ether phosphate in the presence of $Na_2MoO_4$ was observed as is shown in FIG. 11.

In addition to the enol ether phosphate thermal stability evaluation, the reported thermal stabilities for $Na_2MoO_4$, $H_2O_2$ and urea $H_2O_2$ (a common $H_2O_2$ substitute in commercial applications) were examined. Sodium molybdate and hydrogen peroxide did not show any significant thermal decomposition as is shown in Table A.

TABLE A

Evaluation of Oxidation Reagent Thermal Stabilities.

| Reagent | Stability/Storage Conditions |
| --- | --- |
| $H_2O_2$ solution | 35% soln: >99.3% in 1 yr, 25° C.; ≥96.0% in 24 hr, 100° C. |
| Urea $H_2O_2$, solid | Store in dry location away from heat; Store at 15-25° C. |
| Urea $H_2O_2$ buffer, tablet | Store at 2-8° C. |
| $Na_2MoO_4$, solid | "Stable under ordinary conditions of use & storage"; Conditions to avoid: moisture/heat |
| AMPPD-ee | Minimal loss in 1 month, 55° C. |

The stability of the in situ generated dioxetanes, such as AMPPD® and ADP-Star®, is expected to have similar stability to manufactured dioxetanes. The in situ generated dioxetanes can be stored for future use with the usual limitations, e.g., storage at 4° C. for 6 months.

Example 10

Chemiluminescent Assay Design with Enol Ether Substrates—Method A

To adapt in situ 1,2-dioxetane substrate formation to assay design, it is possible to incorporate in situ substrate formation in several ways. For example, the assay can be run where the enzyme activity or enzyme label generates the 1,2-dioxetane substrate precursor (an enol ether phenolate) as the first step, and then the detected signal is generated in the second step with in situ oxidation to the 1,2-dioxetane which upon formation decomposes to give the chemiluminescent signal readout (Method A). In this method, the oxidation step can be thought of as a "stop" solution. Alternatively, the assay can be run where the in situ oxidation of the 1,2-dioxetane precursor to the 1,2-dioxetane is the first step and where enzyme activity or enzyme label generates the 1,2-dioxetane phenolate as the second step (Method B). The second assay method, Method B, where the first step is oxidation, followed by enzyme detection, is described in Section IV (Potential Quenching Effects of $Na_2MoO_4$ and $H_2O_2$ on Alkaline Phosphatase Activity).

Method a (Enzyme Activation Followed by Oxidation):
1) Enzyme activation of enol ether precursor of a 1,2-dioxetane substrate (e.g., by alkaline phosphatase in AMP Buffer to yield a enol ether phenolate).
2) Oxidation of enol ether phenolate (e.g., by $H_2O_2$/$Na_2MoO_4$ in buffer, pH 10).

Figure 12:
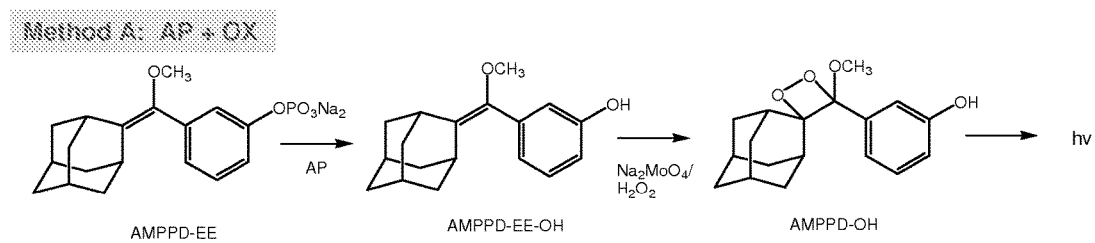
FIG. 12. shows Method A: dephosphorylation of phosphate enol ether (AMPPD-EE) by enzyme followed by aqueous oxidation to dioxetane.

Method A is shown in FIG. 12. In this method, enzyme activation is followed by in situ oxidation to substrate which can be adapted to endpoint assay readouts, where a cumulative signal is measured after enzyme activity. The oxidation to substrate step also functions as an assay stop solution.

Reagents Used:
AMP Buffer: 0.1M aminomethylpropanol buffer, pH 9.8.
TBQ: 10× Sapphire II™ chemiluminescence enhancer (Life Technologies),
AP: Alkaline Phosphatase stock at 8, 1.6, 0.32, 0.064 ng/mL (made from 17.4 mg/mL concentrate),
AMPPD-EE: 1 mg/mL (2.5 mM) in AMP Buffer,
$H_2O_2$ stock: 10% (3M) in water (made from 50% solution, Aldrich),
$Na_2MoO_4$ stock: 0.5M $Na_2MoO_4$ (Aldrich),
Phosphate: 2M $K_2HPO_4$, pH 9.6, and
Control:
10 μL AMPPD® (0.21 mM), 10 μL TBQ, 80 μL AMP Buffer and 10 μL AP (at various concentrations), were combined and the luminescence from the mixture was measured continuously at 37° C. for 30 minutes.

In Situ Oxidation of AMPPD-EE:
10 μL AMPPD-EE (0.21 mM)+10 μL TBQ+[10 μL AP (at various concentrations)+10 μL AMP Buffer, @ 37° C., 1 hour], +[8.5 μL $Na_2MoO_4$ (35 mM)+50 μL Phosphate+25 μL $H_2O_2$ stock (0.63M), sonicate 30 seconds, at 37° C.], 90 minutes, read ~5 minutes (glow).

Figure 13:
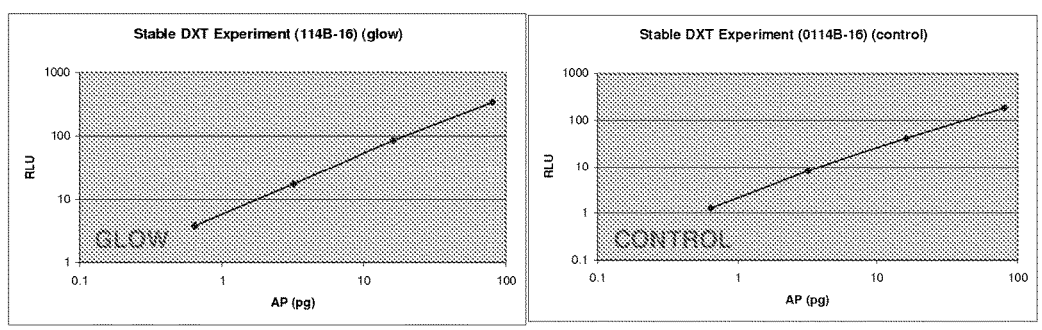
FIG. 13. shows the signal (in relative luminescence units, RLUs) for alkaline phosphatase dilution curves: Glow (in situ AMPPD generated by Method A) vs. Control (AMPPD®) in Method A.
Figure 14:
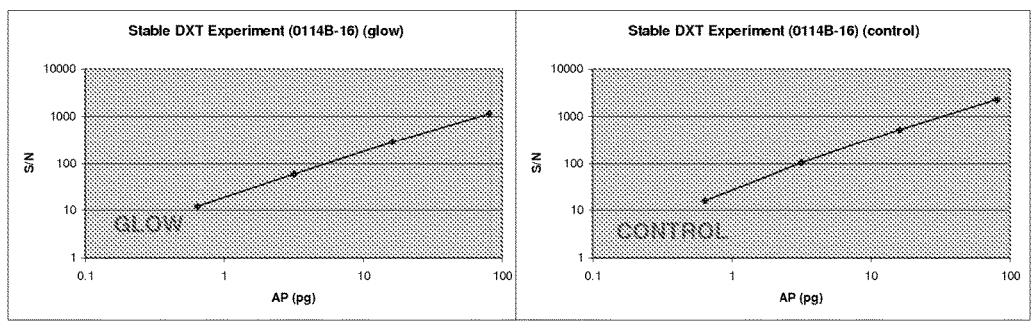
FIG. 14. shows the signal-noise ratio (S/N) for alkaline phosphatase dilution curves: Glow (in situ AMPPD generated by Method A) vs. Control (AMPPD®) in Method A.

Using Method A, AMPPD enol ether phosphate (AMPPD-EE) was 1) dephosphorylated by alkaline phosphatase (across a dilution range) (10 μL AMPPD-EE (0.21 mM)+10 μL TBQ+[10 μL AP (at various concentrations)+10 μL AMP Buffer, @ 37° C., 1 hour]), 2) oxidized in situ to AMPPD® [8.5 μL $Na_2MoO_4$ (35 mM)+50 μL Phosphate+25 μL $H_2O_2$ stock (0.63M), sonicate 30 seconds, at 37° C.], and 3) light emissions from the in situ AMPPD® versus the AMPPD® control, were compared (over 90 minutes, read every 5 minutes). Very similar linear chemiluminescent readouts for the alkaline phosphatase dilution curves were generated from the in situ AMPPD® and the control AMPPD® as is shown in FIG. 13 and FIG. 14.

Example 11

Figure 15:
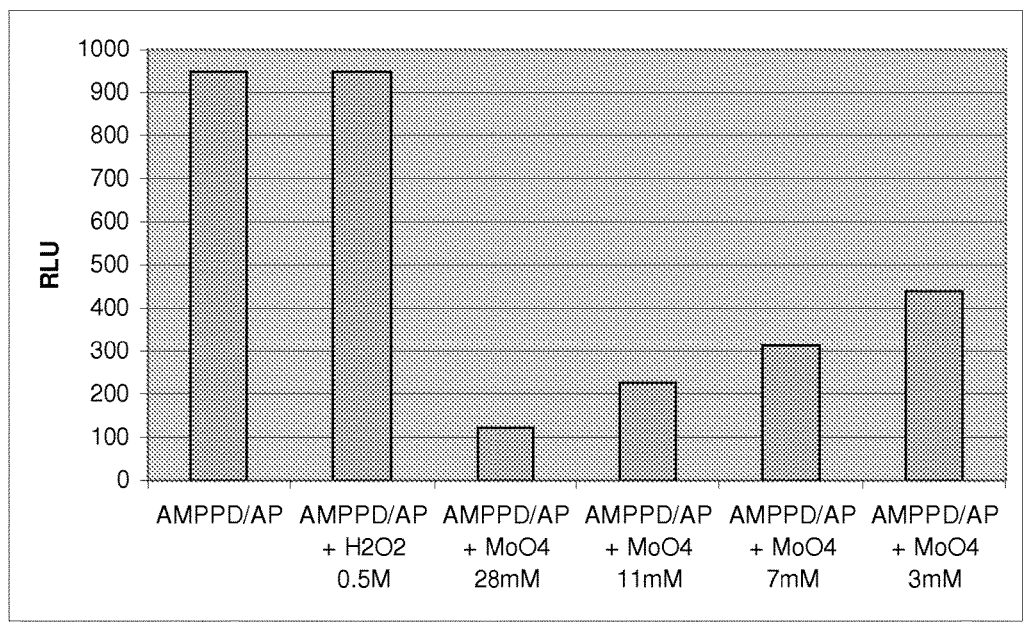
FIG. 15. shows the effects of hydrogen peroxide and sodium molybdate on Enzyme Activity.
Figure 16:
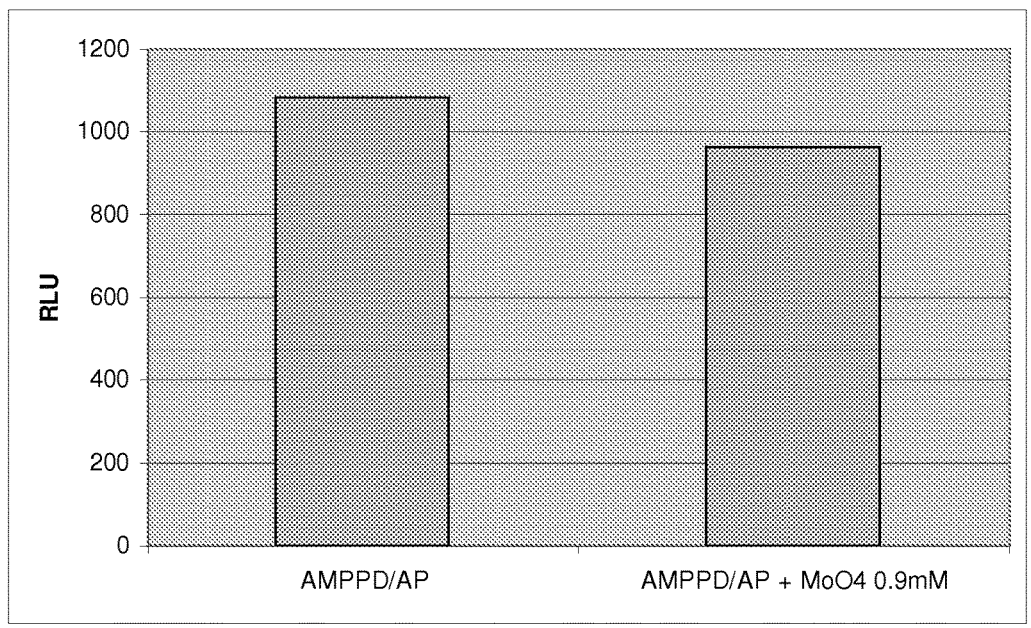
FIG. 16. shows that lowering the sodium molybdate concentration restores enzyme activity.

Potential Quenching Effects of $Na_2MoO_4$ and $H_2O_2$ on Alkaline Phosphatase Activity Before developing assay conditions with Method B in situ dioxetane generation, we investigated whether the reagents from the oxidation system adversely affected alkaline phosphatase activity. Experimental results indicated that hydrogen peroxide does not affect alkaline phosphatase activity, but sodium molybdate significantly quenches alkaline phosphatase activity, with up to 85% light reduction (see FIG. 15). Lowering the concentration of sodium molybdate to <1 mM restores most of the alkaline phosphatase activity (see FIG. 16). Based on these results, Method B in situ dioxetane generation was developed using much lower sodium molybdate concentrations for the oxidation system. Any quenching effects from a singlet oxygen generation/reaction system may be enzyme-specific, and would have to be evaluated for any enzyme/detection substrate pair. For example, $Na_2MoO_4$ quenching may be specific to alkaline phosphatase enzyme and/or related enzyme families, and may not exhibit quenching effects for other hydrolytic enzymes.

Reagents Used:
AMP Buffer: 0.1M aminomethylpropanol buffer, pH 9.8,
AMPPD®: 1 mg/mL AMPPD (Life Technologies) in AMP Buffer
TBQ: 10× Sapphire II™ chemiluminescence enhancer (from Life Technologies),
AP: alkaline phosphatase stock, 40 ng/mL (from 17.4 mg/mL concentrate),
$H_2O_2$ stock: 10% (3M) in water (from 50% solution, Aldrich),
$Na_2MoO_4$ stock: 0.5M (Aldrich), Experimental Conditions:
Control:
10 µL AMPPD® (2.3 mM), 10 µL TBQ, 120 µL AMP Buffer and 10 µL AP (40 ng/mL) were combined and the luminescence from the mixture was measured continuously at 37° C. for 30 minutes.

Tests:
10 µL AMPPD® (2.3 mM), 10 µL TBQ, 80 µL AMP Buffer, 25 µL $H_2O_2$ stock (10%) and 10 µL AP (40 ng/mL) were combined and the luminescence from the mixture was measured continuously at 37° C. for 30 minutes.
10 µL AMPPD® (2.3 mM), 10 µL TBQ, 115 µL AMP Buffer, various amounts of $Na_2MoO_4$ stock and 10 µL AP (40 ng/mL) were combined and the luminescence from the mixture was measured continuously at 37° C. for 30 minutes.

Example 12

Chemiluminescent Assay Design with Enol Ether Substrates—Method B

An alternative approach to incorporating in situ dioxetane substrate generation in an assay oxidizes the enol ether phosphate in the first step, which can be done in an assay well or in a discrete container from which the substrate is added to the assay well. This step is followed by enzyme activation (e.g., dephosphorylation in alkaline phosphatase-based assays) of the in situ dioxetane substrate, with chemiluminescent readout. Method B can be used for kinetic-mode assays to measure assay signal as it is generated. Method B also allows the user to carry out the first step (in situ dioxetane generation) in advance of the assay, if this workflow flexibility is needed.

Method B (Oxidation followed by Enzyme Activation):
1) Oxidation of an enol ether precursor of a 1,2-dioxetane substrate (e.g., by $H_2O_2/Na_2MoO_4$ in buffer, pH 10 to yield the 1,2-dioxetane substrate).
2) Enzyme activation of the in situ generated 1,2-dioxetane substrate (e.g., by alkaline phosphatase in AMP Buffer to yield a 1,2-dioxetane phenolate).

Figure 17:
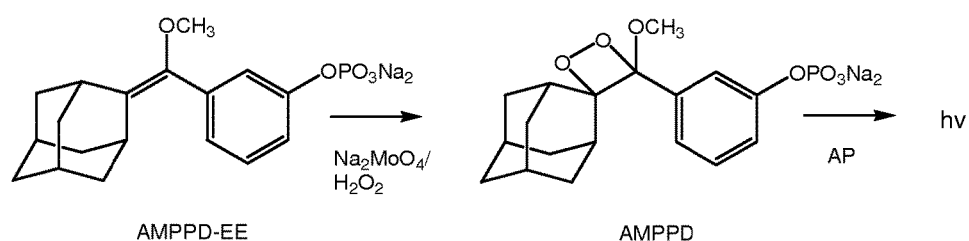
FIG. 17. shows Method B: Aqueous oxidation of AMPPD Enol Ether Phosphate (AMPPD-EE) to dioxetane (in situ AMPPD), followed by enzymatic dephosphorylation.
Figure 18:
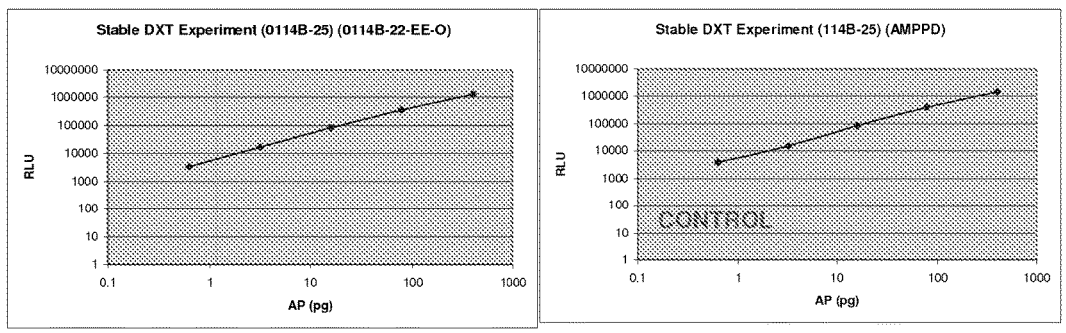
FIG. 18. shows the signal (in RLUs) for alkaline phosphatase dilution curves: in situ AMPPD generated by Method B vs. Control AMPPD®.
Figure 19:
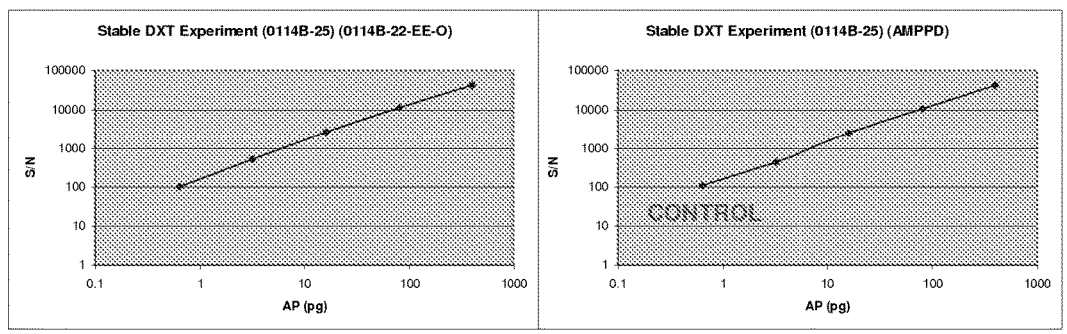
FIG. 19. shows the signal to noise ratio (S/N) for alkaline phosphatase dilution curves: in situ AMPPD generated by Method B vs. Control AMPPD®.

Method B is shown in FIG. 17. In this method, AMPPD enol ether phosphate was oxidized in situ to AMPPD®, dephosphorylated by alkaline phosphatase (across a dilution range), and light emissions from the in situ AMPPD® versus the AMPPD® control, were compared. Again, very similar linear chemiluminescent readouts for the alkaline phosphatase dilution curves were generated from the in situ AMPPD® and the control AMPPD® (see FIG. 18 and FIG. 19). The experimental conditions used are described below.

AMPPD enol ether was oxidized to AMPPD® by combining 200 µL of 5 mg/ml (9 mM) AMPPD-EE in 0.1M aminomethylpropanol buffer, pH 9.8 (AMP Buffer)+5 µL 0.1M $Na_2MoO_4$ (1.8 mM)+75 µL 10% $H_2O_2$ (0.8M) and incubating the mixture at 55° C. for 1 hour. AMP Buffer was the added to a final volume of 1 mL to give a solution containing the oxidized AMPPD-EE (AMPPD-EE-O) at a concentration of ~1 mg/mL (2.5 mM) and 0.5 mM $Na_2MoO_4$. The luminescence properties of AMPP-EE-O was compared to that of AMPPD®.

Reagents Used for Assay:
AMP Buffer: 0.1M aminomethylpropanol buffer, pH 9.8,
AMPPD: 1 mg/mL (2.3 mM) AMPPD (Life Technologies) in AMP Buffer,
AMPPD-EE-O: ~1 mg/mL (2.5 mM) in AMP Buffer,
TBQ: 10× Sapphire II™ chemiluminescence enhancer (Life Technologies),
AP: alkaline phosphatase at concentration of 40, 8, 1.6, 0.32, 0.064 ng/mL (made from 17.4 mg/mL concentrate).

Luminoskan Measurement (Measured in Triplicates):
20 µL (0.46 mM) AMPPD, 10 µL TBQ, 60 µL AMP Buffer and 10 µL AP (4, 0.8, 0.16, 0.032, 0.0064 ng/mL) were combined and the luminescence from the mixture was measured continuously at room temperature for 2 hours.
20 µL AMPPD-EE-O (0.5 mM), 10 µL TBQ, 60 µL AMP Buffer and 10 µL AP (4, 0.8, 0.16, 0.032, 0.0064 ng/mL) were combined and the luminescence from the mixture was measured continuously at room temperature for 2 hours.

Method B was also used to evaluate in situ generation of ADP-Star® from ADP-Star enol ether phosphate as discussed previously. The light emission curves from in situ ADP-Star® and control ADP-Star, as shown in FIG. 7, are superimposable. A modification of Method B to accommodate ADP-Star enol ether phosphate solubility was done as described below.

Reagents Used:
Solution A: 23.3 mM ADP-Star-EE in 30% acetonitrile/70% sodium carbonate solution*, with 12.5 mM $Na_2MoO_4$.
Solution B: 10% $H_2O_2$.
*Sodium carbonate solution: 32 gm sodium bicarbonate+12 gm sodium carbonate in 10 liters water
1 mL Solution A and 0.7 ml Solution B were combined and heated at 55° C. for 15 minutes (until color disappears) to generate 13.7 mM in situ ADP-Star stock solution.

Figure 20:
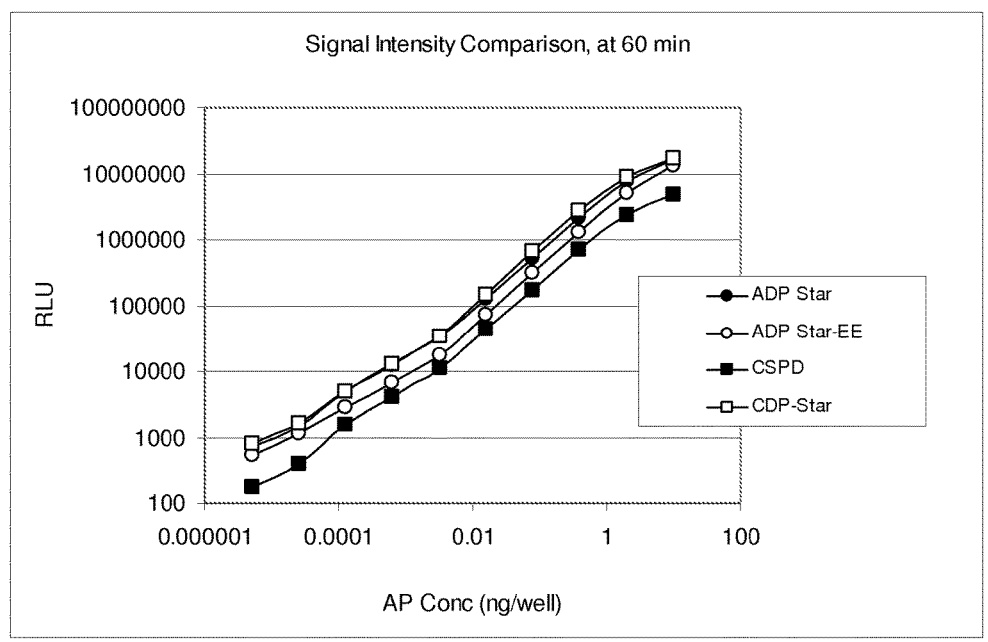
FIG. 20 shows the signal (in RLUs) for alkaline phosphatase dilution curves: in situ ADP-Star (ADP-Star-EE) generated by Method B vs. CSPD®, ADP-Star® and CDP-Star® controls.
Figure 21:
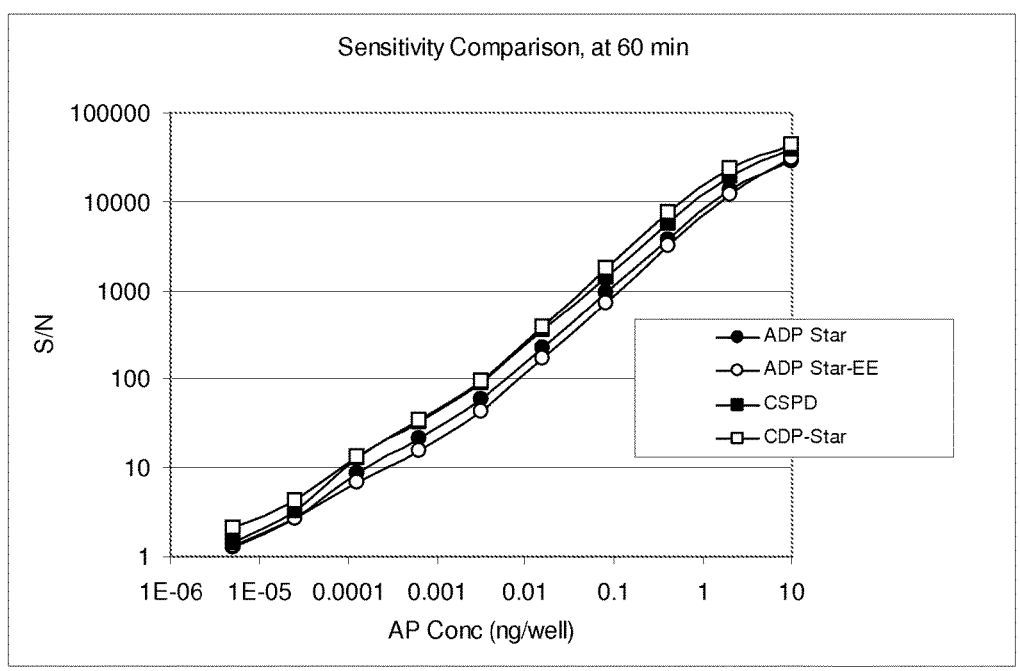
FIG. 21 shows the signal to-noise ratio (S/N) for alkaline phosphatase dilution curves: in situ ADP-Star (ADP-Star-EE) generated by Method B vs. CSPD®, ADP-Star® and CDP-Star® controls.

Tests:
1.7 mL of in situ ADP-Star stock solution was combined with 56.3 mL 0.1M aminomethylpropanol buffer, pH 9.5 and 1 mg/mL Sapphire II™ chemiluminescence enhancer (Life Technologies), to generate a solution containing 0.4 mM in situ ADP-Star and 1 mg/ml Sapphire II™. The performance of in situ generated ADP-Star, compared with dioxetane controls CSPD, ADP-Star and CDP-Star in alkaline phosphatase dilution curves, was similar to the control dioxetanes (see FIG. 20 and FIG. 21).

Generation of similar enzyme dilution curves with in situ generated AMPPD and control AMPPD, using two different assay/substrate generation methods (Method A and Method B) demonstrates that the principle of in situ dioxetane substrate generation can be readily adapted to enzyme assay applications. Comparable results were obtained using Method B for in situ ADP-Star and control dioxetanes, CSPD® (Life Technologies), ADP-Star® and CDP-Star®. These substrate generation and assay design principles were demonstrated with alkaline phosphatase substrates and assays, but can be generally adapted to dioxetane substrates and assays for other hydrolytic enzymes, such as β-galactosidase, β-glucuronidase, β-glucosidase and neuraminidase.

Example 13

Model Recombinant Human Interleukin 6 (rhIL-6) ELISA with Enol Ether Substrates 1. rhIL-6 ELISAs with In Situ AMPPD Detection.

Figure 22:
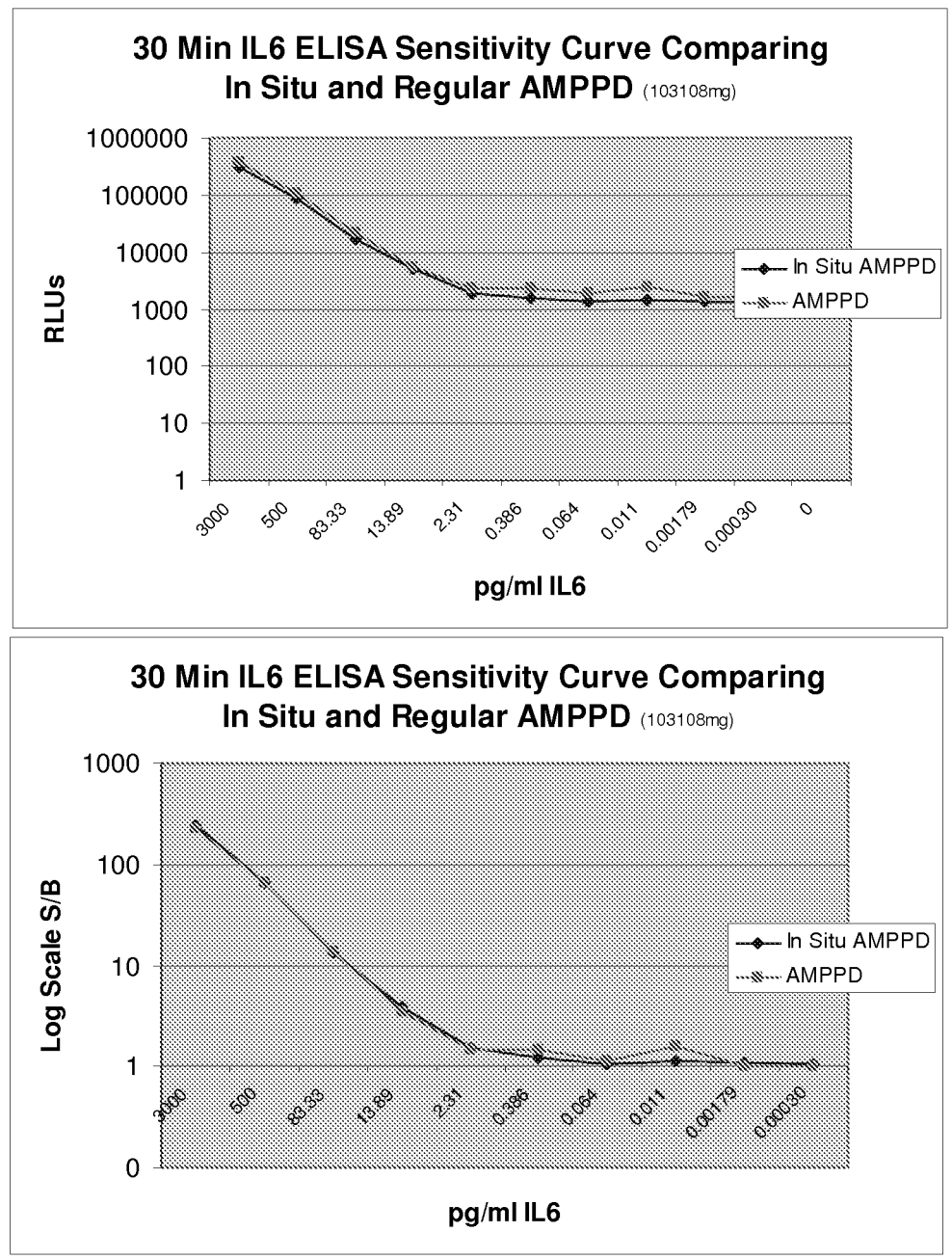
FIG. 22. shows the 30-minute IL-6 ELISA sensitivity curves: in situ AMPPD vs. control AMPPD®.

Model recombinant rhIL-6 detection ELISAs were run side by side with in situ AMPPD and control AMPPD®, to evaluate the performance of in situ AMPPD in an immunoassay. Experiments showed that AMPPD generated in situ performed as well as control AMPPD® in the assay using "equal" molar amounts of substrate, assuming 100% conversion of the enol ether phosphate (See FIG. 22). The in situ AMPPD could be prepared during ELISA incubation steps, did not add extra time to the assay, and was not any more inconvenient than the ELISA assay itself. The overall assay sensitivity and dynamic range compared well to internal rhIL-6 ELISAs detected with CDP-Star® (CDP*).

rhIL-6 ELISA Plate Prep (96-Well Microtiter Plate):
1. Coat ELISA plate overnight w/capture antibody (2 mg/mL anti-human IL-6).
2. Wash plate well.
3. Block plates with 300 µL/well blocking buffer (1×PBS/ 0.02% Tween 20/1% BSA).
4. Wash plate well.

rhIL-6 Assay:
5. Add 100 µL of samples or standards (3000 pg/µL- 0.0003 pg/mL of rhIL-6, w/1:6 dilutions) to wells and let incubate at room temp for 30 minutes.
6. Wash plate well
7. Add 100 µL of 12.5 ng/ml of biotinylated detection anti-IL6 antibody (R&D Systems) and incubate at room temp for 15 minutes Wash plate well.
8. Add 100 µL of alkaline phosphatase-conjugated Streptavidin (Jackson Laboratories) at 1:40,000 dilution.
9. Wash plate well.
10. Add 100 ul of Substrate Solution to each well, and incubate for 30 min room temp.
11. Measure RLU of each well at 30 minutes, with temperature at 25° C., using a luminometer.

In situ Dioxetane Preparation of AMPPD:
Solution A was prepared by combining the below solution to give a stock solution of AMPPD Enol Ether Phosphate at 12.7 mM.

5 mg/mL AMPPD Enol Ether Phosphate (from Example 2; MW 394).
2 mL 0.1M aminomethylpropanol buffer, pH 9.8 (AMP Buffer).
50 µL 0.1M Na$_2$MoO$_4$ Step 1—Made Solution B.
100 µL Solution A
38 µL 10% H$_2$O$_2$ (makes 9.2 mM AMPPD®, MW 426)
Heat solution at 55° C. for 1 hour (O$_2$ bubbles outgas, color change to clear)
This is Solution B. A chemiluminescence enhancer can also be added at this step.

Step 2 (2.54 mM)—Made Solution C at 2.54 mM AMPPD.
138 µL Solution B (has 9.2 mM AMPPD®, generated in situ)
362 µL 0.1M AMP Buffer, pH 9.8
This is Solution C, at 2.54 mM AMPPD®.

Step 2 (4 mM)—Made Solution C at 4 mM AMPPD.
138 µL Solution B (has 9.2 mM AMPPD®, generated in situ)
149.4 µL 0.1M AMP Buffer, pH 9.8
This is Solution C, at 4 mM AMPPD®.

Step 3 (0.25 mM)—Made Solution D at 0.25 mM AMPPD.
1 mL Solution C (2.54 mM AMPPD®)
1 mL 10× Sapphire II (Life Technologies)
8 mL 0.1M AMP Buffer, pH 9.8
This is Solution D, at 0.25 mM AMPPD®
Add 100 µL of Solution D to each well.

*Step 3 (0.4 mM)—Made Solution D at 0.4 mM AMPPD.
1 ml Solution C (4 mM AMPPD®)
1 ml 10× Sapphire II (Life Technologies)
8 ml 0.1M AMP Buffer, pH 9.8
This is Solution D, at 0.4 mM AMPPD®
Add 100 µL of Solution D to each well.

Figure 23:
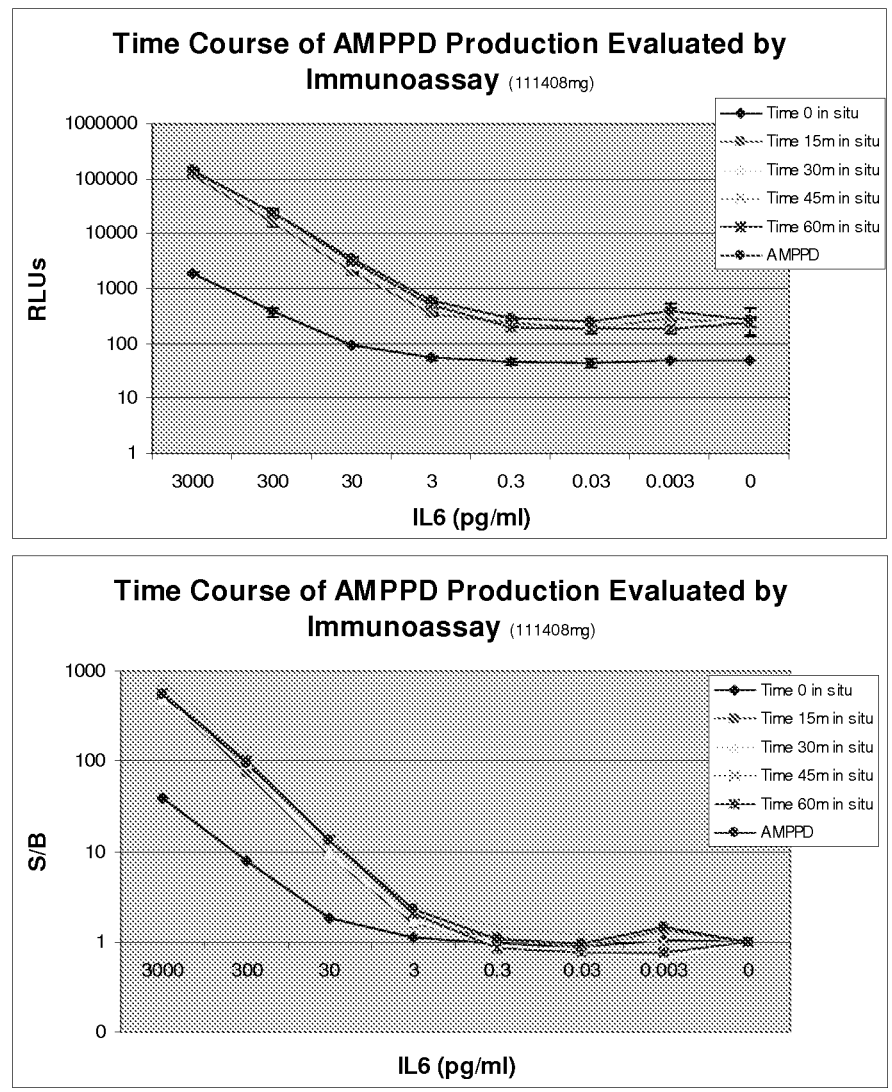
FIG. 23 shows the time course of in situ AMPPD production, evaluated by IL-6 ELISAs.

*This sets up comparative assay conditions, since a standard assay detection is with 0.4 mM 1,2-dioxetane & 1 mg/ml enhancer In another set of experiments, the oxidation time to generate in situ AMPPD was varied, and then substrate performance was evaluated by rhIL-6 ELISAs, with control AMPPD®. Time course experiments showed that by 30 minutes most of the AMPPD Enol Ether Phosphate appeared to be converted to in situ AMPPD. There was very little compromise in immunoassay performance (sensitivity and dynamic range) using 15 minute in situ generated AMPPD vs 60 minute in situ generated AMPPD. There was also very little difference in detection signal (RLUs) with 30 minute in situ generated AMPPD vs 60 min in situ generated AMPPD. Some conversion of AMPPD enol ether phosphate to in situ AMPPD likely occurs during the assay as indicated by T$_o$ results (see FIG. 23).

2. rhIL-6 Detection ELISAs with in situ ADP-Star Detection.

Figure 24:
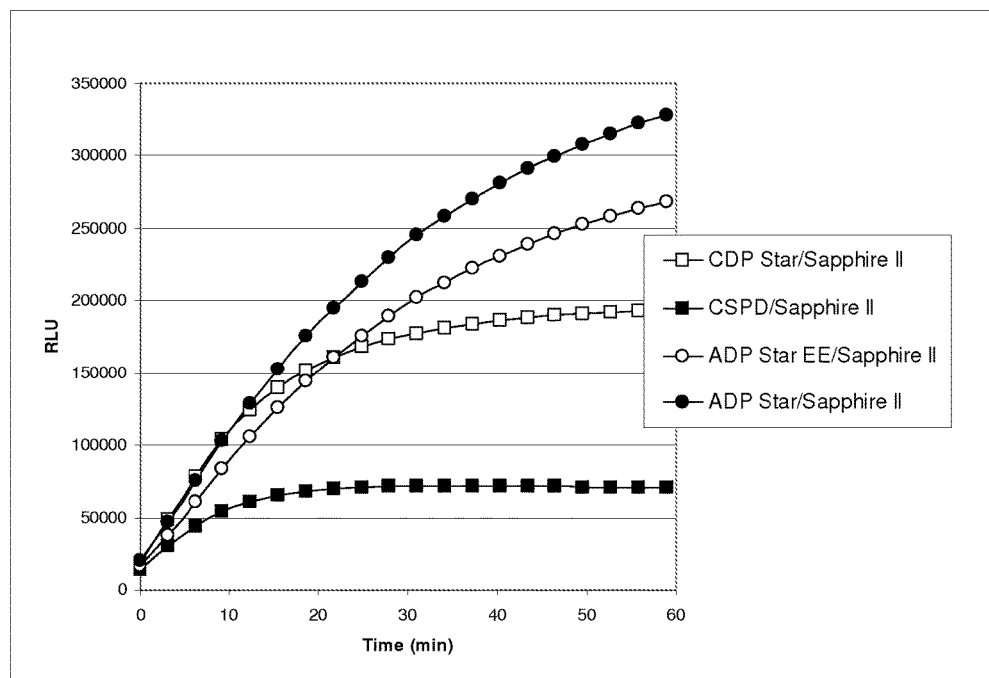
FIG. 24. shows the light emission curves for in situ ADP-Star (ADP Star EE) vs. control ADP-Star®, CDP-Star®, and CSPD®, in the presence of the chemiluminescence enhancer, Sapphire II™.
Figure 25:
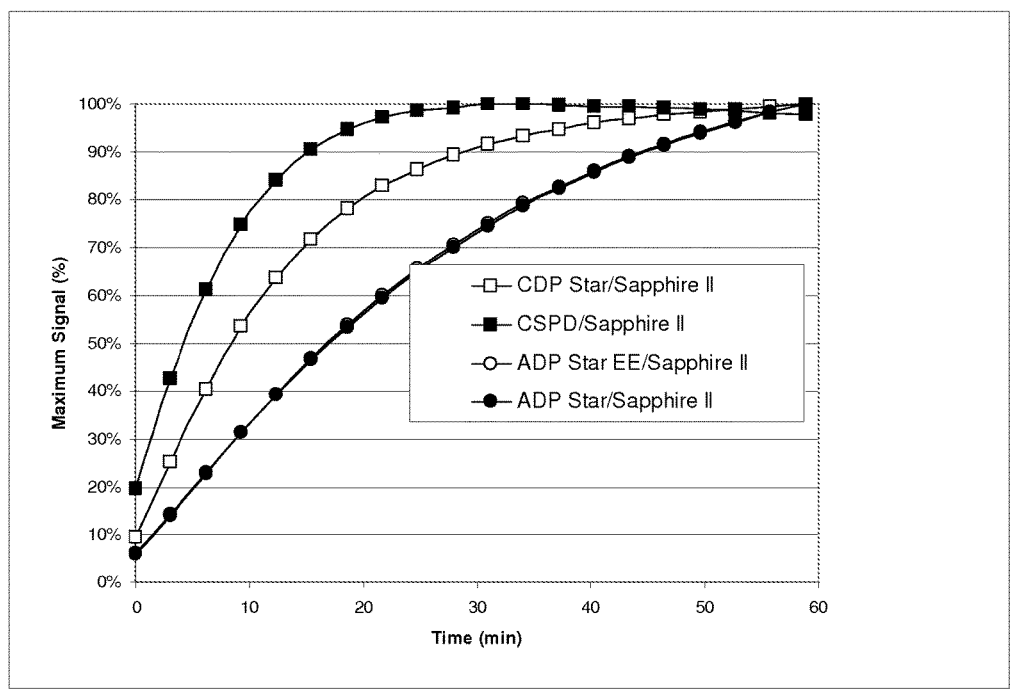
FIG. 25 shows the maximum light signal curves (%) over time for in situ ADP-Star (ADP Star EE) vs. control dioxetanes, CSPD®, ADP-Star®, and CDP-Star®, in the presence of the chemiluminescence enhancer, Sapphire II™.

Benchmarking experiments compared the light emission (in RLUs) and signal to noise (S:N) of in situ ADP-Star with control dioxetanes CSPD®, ADP-Star®, and CDP-Star®. Maximum light emission varied with dioxetane substrates, with CSPD® reaching glow at 30 minutes, CDP-Star® reaching glow at 45 minutes, and ADP-Star® reaching glow at 60 minutes (see FIG. 24 and FIG. 25).

Figure 26:
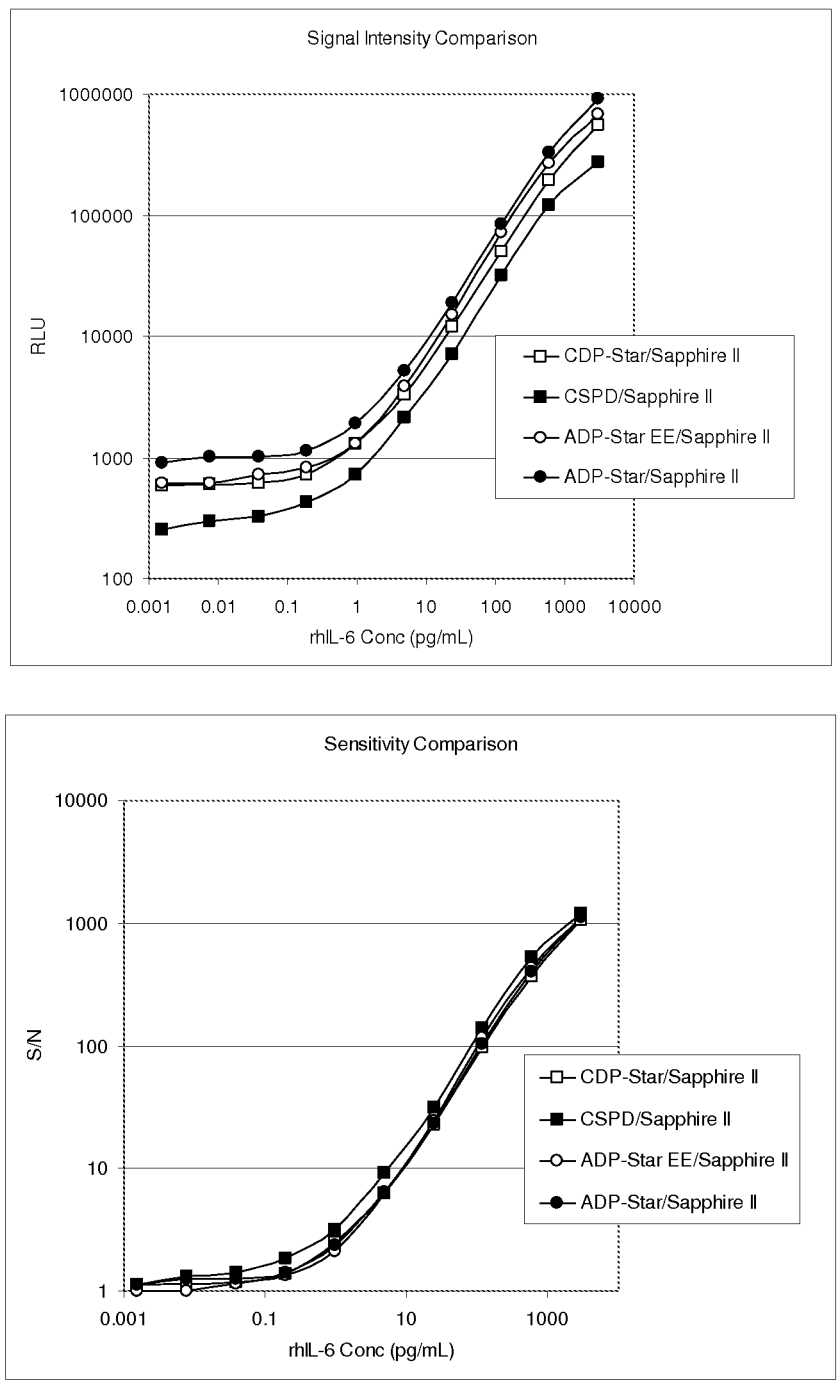
FIG. 26. shows the rhIL-6 ELISA detection curves: in situ ADP-Star (ADP-Star EE) vs. control dioxetanes, CSPD®, ADP-Star® and CDP-Star®, in the presence of the chemiluminescence enhancer, Sapphire II™.

Model rhIL-6 ELISAs were run side by side with in situ ADP-Star, and control dioxetanes CSPD®, ADP-Star® and CDP-Star®, to evaluate the performance of in situ ADP-Star in an immunoassay. Experiments showed that ADP-Star generated in situ performed comparably to control dioxetane substrates. The assay sensitivity (lower end detection of IL-6), S/N, and dynamic range were similar for all substrates, including the in situ generated ADP-Star (see FIG. 26).

Figure 27:
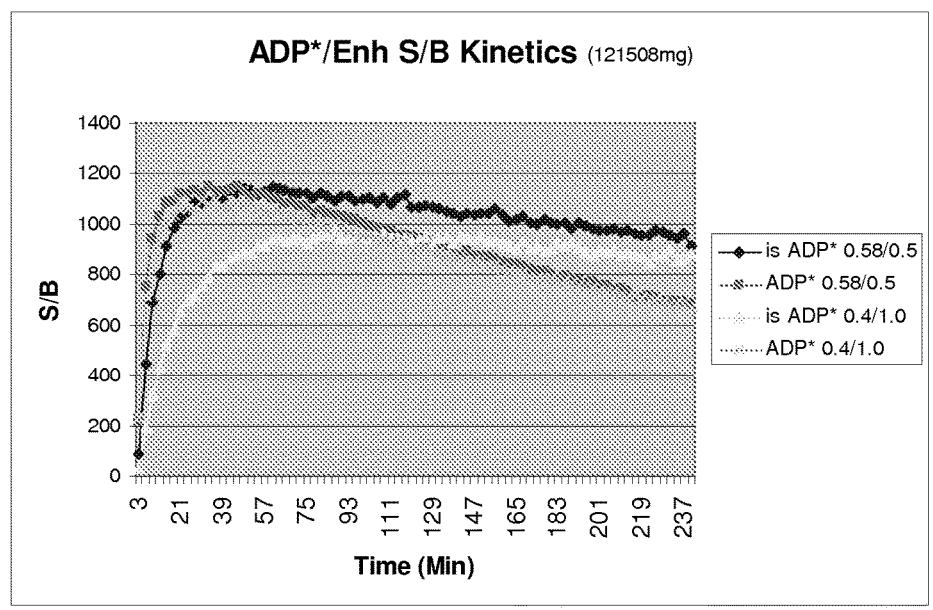
FIG. 27. shows the signal to background (S/B) kinetics for ADP-Star (ADP*), generated in situ, in the presence of TBQ enhancer (poly[vinyl(benzyltributylammonium chloride)]).
Figure 28:
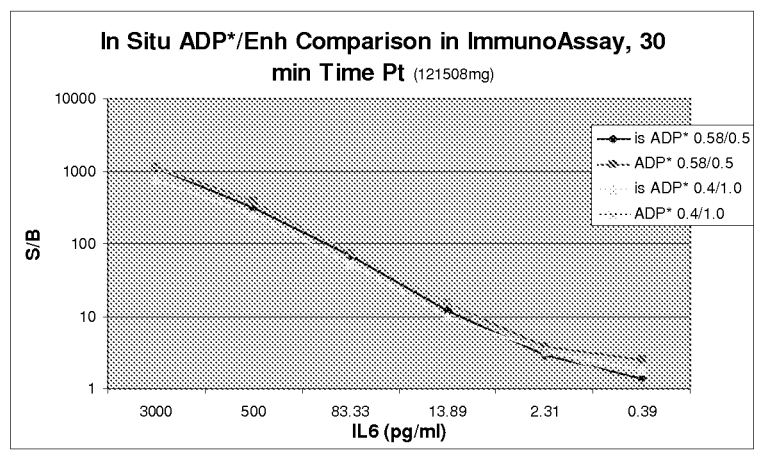
FIG. 28. shows the IL-6 ELISA sensitivity comparison at a 30-minute time point for ADP-Star (ADP*), generated in situ, in the presence of TBQ Enhancer.
Figure 29:
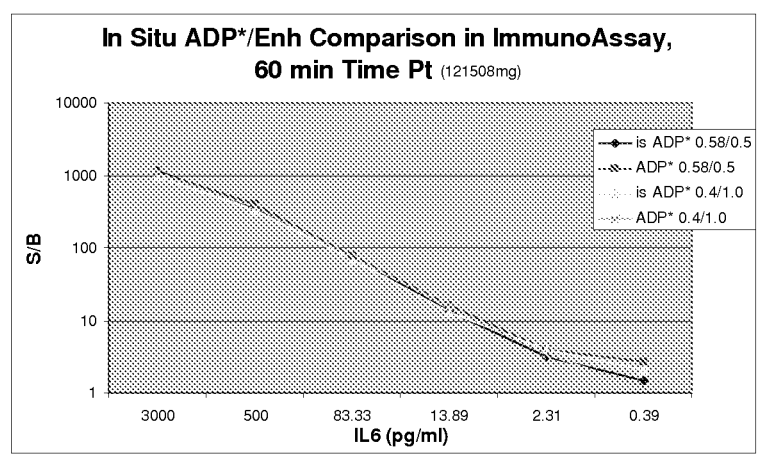
FIG. 29. shows the IL-6 ELISA sensitivity comparison at a 60 minute time point ADP-Star (ADP*), generated in situ, in the presence of TBQ Enhancer.

It may be desirable in application development to eliminate one or more of the solution preparation steps A-D described above. It may also be desirable in certain applications to modify solution components. An example of modified solution components was demonstrated by preparation of the detection solution, with the enhancer present in the oxidation step, prior to dilution with buffer to assay conditions. Using the modified in situ dioxetane preparation, alkaline phosphatase detection curves show similar sensitivity with in situ ADP-Star (dark blue and yellow light emission curves), compared to ADP-Star® controls (red and light blue emission curves) (see FIG. 27). In fact, the in situ ADP-Star detection solution gives steadier light emission upon reaching emission maximum, compared to the controls. In addition, the modified in situ ADP-Star dioxetane preparation gives immunoassay detection sensitivity comparable to control dioxetanes for an IL-6 ELISA (see FIG. 28 and FIG. 29).

ADP-Star Generated In Situ in Enhancer Solution:
a) Oxidation performed at 11.7 mM ADP-Star Enol Ether Phosphate (from Example 3) and 10 mg/ml Sapphire II (Life Technologies) in AMP Buffer+Na$_2$MoO$_4$. After oxidation, the solution is diluted to 1× with AMP Buffer. Final solution concentration: 0.58 mM in situ generated ADP-Star/0.5 mg/ml Sapphire II.
b) Oxidation performed at 4 mM ADP-Star Enol Ether Phosphate (from Example 3) and 10 mg/ml Sapphire in AMP Buffer+Na$_2$MoO$_4$. After oxidation, solution diluted to 1× with AMP Buffer. Final: 0.4 mM in situ generated ADP-Star/1 mg/ml Sapphire II.

Having described specific embodiments of the present invention with reference to the accompanying drawings, it will be appreciated that the present invention is not limited to those precise embodiments, and that various changes and modifications can be effected therein by one of ordinary skill in the art without departing from the scope or spirit of the invention as defined by the appended claims.

We claim:
1. A method for generating light comprising:
a) providing an oxidant selected from the group consisting of at least one of hydrogen peroxide, sodium molybdate, hydrogen peroxide and sodium molybdate, hypochlorite, hypochlorite and hydrogen peroxide, aryl endoperoxide, calcium peroxide peroxyhydrate, and combinations thereof,
b) providing an enol ether having the structure:

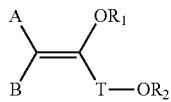

in which,
A and B together is

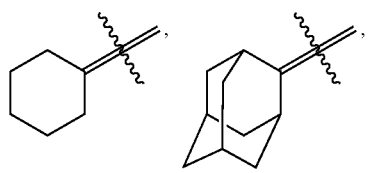

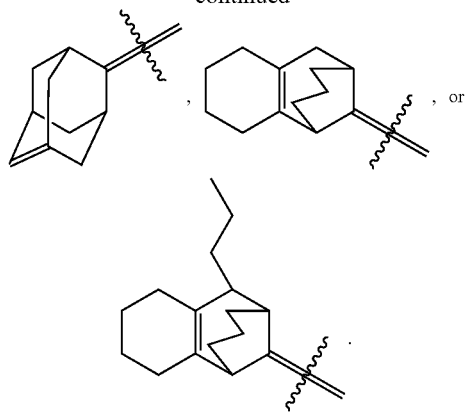

$R_1$ is alkyl containing 1 to 20 carbon atoms, aryl containing 6 to 14 carbon atoms, aralkyl containing 7 to 15 carbon atoms, heteroaryl containing 4 to 20 carbon atoms, or heteroaralkyl containing 5 to 20 carbons, T is an aryl or heteroaryl ring capable of emitting light, and
R2 is an enzyme-cleavable group that contains a bond cleavable by an enzyme moiety to yield an oxygen anion on T and wherein T-OR$_2$ is

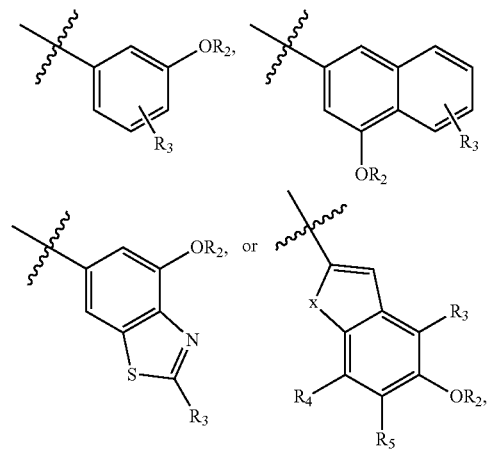

wherein, $R_3$, $R_4$, and $R_5$, are independently selected from the group consisting of H, F, Cl, Br, I, cyano, nitro, sulfonate, sulfate, trifluomethyl, trifluroethyl, straight chain alkyl containing 1 to 20 carbon atoms, branched alkyl containing 3 to 20 carbon atoms, straight chain alkenyl containing 2 to 20 carbon atoms, branched alkenyl containing 3 to 20 carbon atoms, cycloalkyl containing 3 to 20 carbon atoms, cycloalkenyl containing 3 to 20 carbon atoms, cycloheteroalkyl containing 3 to 20 carbon atoms, cycloheteroalkenyl containing 3 to 20 carbon atoms, polycycloalkyl containing 4 to 60 carbon atoms, polycycloalkenyl containing 4 to 60 carbon atoms, polycycloheteroalkyl containing 4 to 60 carbon atoms, polycycloheteroalkenyl containing 4 to 60 carbon atoms, alkoxy containing 1 to 20 carbon atoms, aryl containing 6 to 14 carbon atoms, aryloxy containing 6 to 14 carbon atoms, ester containing 2 to 21 carbon atoms, trialkylammonium containing 3 to 30 carbon atoms, trialkylphosphonium containing 3 to 30 carbon atoms, alkylamido containing 2 to 21 carbon atoms, arylamido containing 7 to 15 carbon atoms, alkylcarbamoyl containing 2 to 21 carbon atoms, arylcarbamoyl containing 7 to 15 carbon atoms, alkylsulfonamido containing 1 to 20 carbon atoms, arylsulfonamido containing 6 to 14 carbon atoms, trialkylsilyl containing 3 to 60 carbon atoms, triarylsilyl containing 18 to 42 carbon atoms, alkylarylsilyl containing 7 to 32 carbon atoms, alkylamidosulfonyl containing 1 to 20 carbon atoms, arylamidosulfonyl containing 6 to 14 carbon atoms, alkylsulfonyl containing 1 to 20 carbon atoms, arylsulfonyl containing 6 to 14 carbon atoms, alkylthio containing 2 to 20 carbon atoms and arylthio containing 6 to 14 carbon atoms, and X is a sulfur atom, oxygen atom, or nitrogen atom;

(c) combining an aqueous solution comprising aminomethylpropanol at alkaline pH, the oxidant, and the enol ether to generate in situ a 1,2-dioxetane enzyme substrate in the aqueous solution;

(d) providing an enzyme complex comprising an enzyme which is capable of cleaving the in situ generated 1,2-dioxetane enzyme substrate;

(e) contacting the enzyme complex with the aqueous solution comprising the in situ generated 1,2-dioxetane enzyme substrate obtained in step (c) to form a reaction mixture; and, (f) allowing the reaction mixture to generate light.

2. The method of claim 1, wherein $R_1$ is alkyl containing 1 to 2 carbon atoms or trifluoalkyl containing 1 to 2 carbon atoms.

3. The method of claim 1, wherein $OR_2$ is phosphate, acetate, 1-phospho-2,3-diacylglyceride, adenosine triphosphate, adenosine diphosphate, adenosine monophosphate, adenosine, α-D-galactoside, β-D-galactoside, α-D-glucoside, β-D-glucoside, α-D-mannoside, β-D-mannoside, β-fructofuranoside, β-D-glucuronide, or

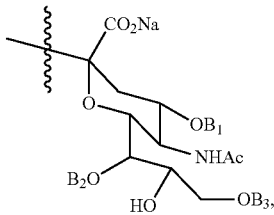

wherein, $B_1$, $B_2$ and $B_3$ are each independently H or an alkyl (branched or straight chain) of 1-4 carbon atoms.

4. The method of claim 3, wherein $R_2$ is

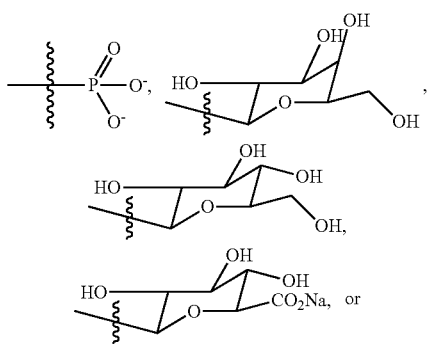

5. The method of claim 1, wherein $R_2$ is E-L-Nuc-Z, wherein E is a group comprising an electrophilic atom, which atom upon the enzymatic cleavage of the Z group is attacked by the electron pair of the Nuc group and by anchimeric assistance releases the 1,2-dioxetane enzyme substrate anion; L is a linking group; Nuc is nucleophic atom; and Z is an enzymatically cleavable group; wherein E is carboxyl, carbonyl, methylene substituted by a leaving group, phosphate, carbonate, xanthate, sulfite, sulfonate, bisulfate or bisulfide;

L is selected from the group consisting of methylene or polymethylene containing 1 to 4 carbon atoms, $-(CH_2)_m-O-(CH_2)_n-$, $-(CH_2)_m-S-(CH_2)_n-$, or $(CH_2)_m-NR_6-(CH_2)_n-$, wherein m and n are 0 to 3 and m+n is 2 or 3, wherein $R_6$ is alkyl containing 1 to 10 carbon atoms and the linking group may be substituted by alkyl containing 1 to 24 carbon atoms, alkenyl containing 2 to 24 carbon atoms, alkyl containing 1 to 24 carbon atoms and mono- or di-substituted with acyloxy containing 1 to 24 carbon atoms, alkenyl containing 2 to 24 carbon atoms and mono- or disubstituted with acyloxy containing 1 to 24 carbon atoms, aryl containing 6 to 10 carbons, alkyl containing 1 to 24 carbon atoms and substituted with phenyl, hydroxyphenyl, indolyl, mercapto, alkylthio containing 1 to 4 carbon atoms, hydroxy, carboxy, amino, guanidino, imidazole or carbamyl, or alkenyl containing 2 to 24 carbon atoms and substituted with phenyl, hydroxyphenyl, indolyl, mercapto, alkylthio containing 1 to 4 carbon atoms, hydroxy, carboxy, amino, guanidino, imidazole, or carbamyl;

Nuc is an oxygen atom or sulfur atom; and

Z is phosphoryl, acetyl, 1-phospho-2,3-diacylglycerosyl, adenosine triphosphoryl, adenosine diphosphoryl adenosine monophosphoryl, adenosyl, α-D-galactosyl, β-D-galactosyl, α-D-glucosyl, β-D-glucosyl, α-D-mannosyl, β-D-mannosyl, β-fructofuranosyl, β-D-glucosiduransyl, or

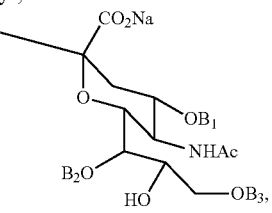

wherein, $B_1$, $B_2$ and $B_3$ are each independently H or an alkyl (branched or straight chain) of 1-4 carbon atoms.

6. The method of claim 5, wherein Z is

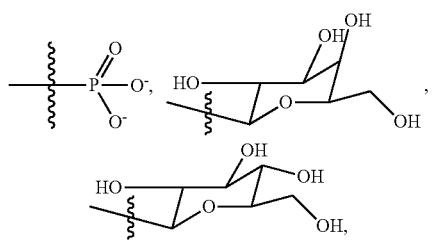

-continued

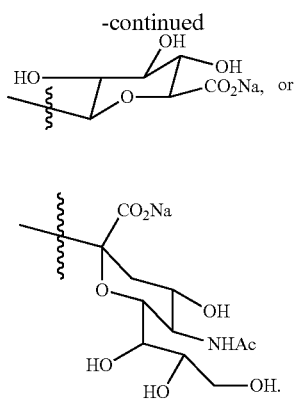

7. The method of claim 1, wherein the enzyme comprises a hydrolyic enzyme selected from alkaline phosphatase, β-galactosidase, β-glucosidase, β-glucuronidase, or neuraminidase.

8. The method of claim 1 further comprising the step of detecting the generated light.

9. The method of claim 1, wherein the enzyme comprises an enzyme-linked antibody comprising a first antibody capable of binding to an antigen and an enzyme moiety; an enzyme-linked antigen comprising an antigen and an enzyme; or an enzyme-linked oligonucleotide comprising an oligonucleotide capable of hybridizing to a nucleic acid, wherein the enzyme moiety is capable of cleaving the 1,2-dioxetane enzyme substrate so that the substrate decomposes and generates light.

10. The method of claim 9, wherein the first antibody or antigen is covalently linked to a label and the enzyme is covalently linked to a molecule capable of non-covalent binding to the label.

11. The method of claim 9, further comprising the steps of:
 (a) providing a sample suspected of comprising an antigen;
 (b) providing a solid phase comprising a second antibody capable of binding to the antigen;
 (c) contacting the sample and enzyme-linked antibody with the solid phase to form the enzyme complex; and,
 (d) detecting the light emitted following cleavage of said 1,2-dioxetane enzyme substrate.

12. The method of claim 7, further comprising the steps of:
 (a) providing a sample suspected of comprising an antigen;
 (b) providing a solid phase comprising an antibody capable of binding to the antigen;
 (c) contacting the sample and enzyme-linked antigen with the solid phase to form an enzyme complex; and,
 (d) detecting the light emitted following cleavage of said 1,2-dioxetane enzyme substrate.

13. The method of claim 9, wherein oligonucleotide is covalently linked to a label and the enzyme is covalently linked to a molecule capable of non-covalent binding to the label.

14. The method of claim 1, wherein said aqueous solution further comprises an enhancer.

15. The method of claim 14, wherein the enhancer comprises a polymeric quaternary ammonium salt, polymeric quaternary phosphonium salt, an acceptor dye and a combination thereof.

16. The method of claim 1, wherein the enol ether is

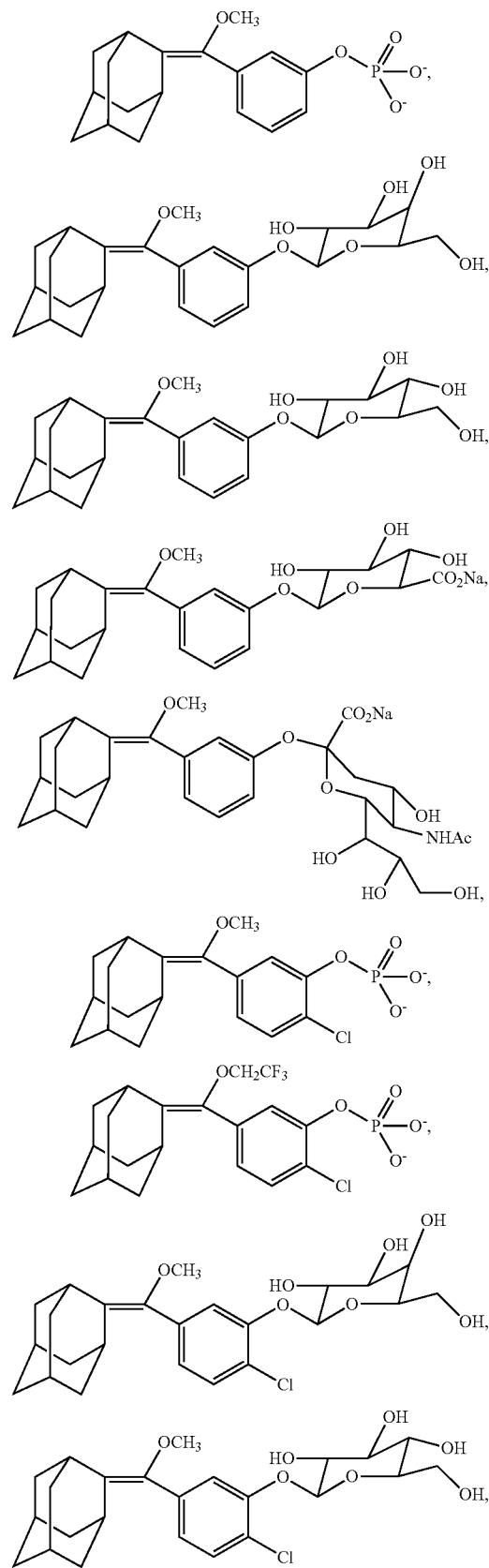

51
-continued
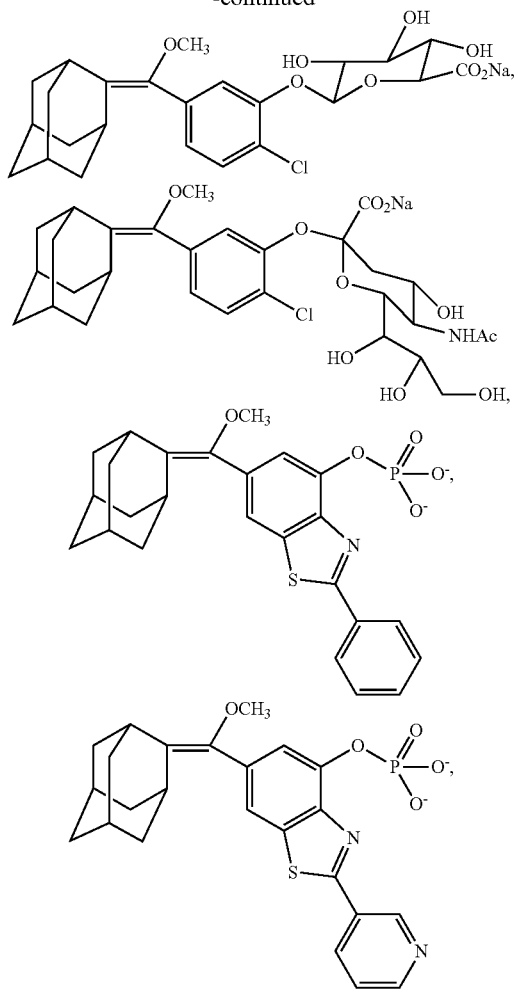
52
-continued
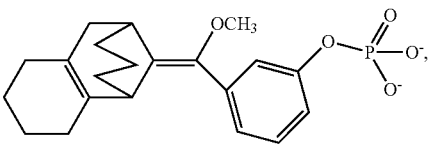
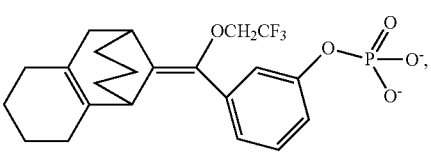
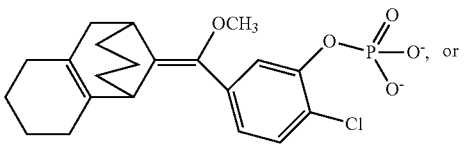, or
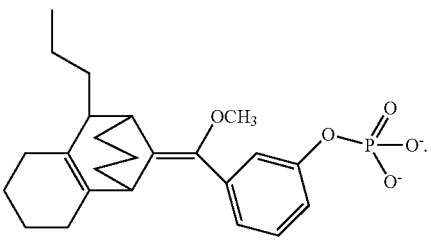
* * * * *